United States Patent [19]

Kiely et al.

[11] Patent Number: 4,602,023

[45] Date of Patent: Jul. 22, 1986

[54] DIPHENIC ACID MONOAMIDES

[75] Inventors: John S. Kiely, Ann Arbor; Suchin Huang, Canton, both of Mich.

[73] Assignee: Warner-Lambert Company, Morris Plains, N.J.

[21] Appl. No.: 740,799

[22] Filed: Jun. 3, 1985

[51] Int. Cl.⁴ .................... A61K 31/44; A61K 31/40; A61K 31/19; C07C 103/84
[52] U.S. Cl. ............................... 514/346; 260/501.11; 260/501.15; 260/501.17; 514/354; 514/355; 514/357; 514/423; 514/424; 514/427; 514/466; 514/471; 514/555; 514/563; 546/291; 546/315; 546/328; 546/335; 548/540; 548/550; 548/556; 548/567; 549/441; 549/475; 549/478; 549/488; 549/493; 562/441; 562/455; 562/456; 562/457

[58] Field of Search ............... 260/501.11, 501.15, 260/501.17; 562/441, 455, 456, 457; 546/291, 315, 328, 335; 548/540, 550, 556, 567; 549/441, 475, 478, 488, 493; 514/555, 563, 346, 354, 355, 357, 423, 424, 427, 466, 471

[56] References Cited

U.S. PATENT DOCUMENTS 3,995,045  11/1976  Wade et al. ..................... 546/335

Primary Examiner—Dolph H. Torrence
Attorney, Agent, or Firm—Joan Thierstein

[57] ABSTRACT

The present invention provides various novel diphenic acid monoamide compounds, novel pharmaceutical compositions and methods of use thereof, as well as novel methods of synthesis therefor. The novel diphenic acid monoamides of the present invention are leukotriene antagonists, 5-lipoxygenase inhibitors, and mediator release inhibitors providing activity useful for treating asthma, allergies, cardiovascular diseases, migraines, and immunoinflammatory conditions.

31 Claims, No Drawings

DIPHENIC ACID MONOAMIDES

BACKGROUND OF THE INVENTION

The present invention provides various novel diphenic acid monoamide compounds, novel pharmaceutical compositions, and methods of use thereof, as well as, novel methods of synthesis therefor. The novel diphenic acid monoamides of the present invention are leukotriene antagonists, 5-lipoxygenase inhibitors, and mediator release inhibitors providing activity useful for treating asthma, allergies, cardiovascular diseases, migraines, and immunoinflammatory conditions.

It is disclosed in U.S. Pat. No. 3,995,045 that 2'-[3,6-dihydro-4-phenyl-1(2H)-pyridinyl or phenyl-1-piperidinyl)alkyl-aminocarbonyl] [1,1'-diphenyl]-2-carboxylic acids are useful as antiinflammatory agents and, further, are useful in the prevention and inhibition of granuloma formation. Among the differences between the invention in U.S. Pat. No. 3,995,045 and the present invention are notably the presence of a pyridinyl or piperidinyl ring attached to an alkyl of an alkylaminocarbonyl group as well as various combination of substituents of aryls all of which are not the present invention.

SUMMARY OF THE INVENTION

The present invention is a compound of Formula I wherein $R_1$ is hydrogen or lower alkyl of from one to four carbons, inclusive; B is (a) —$(CH_2)_m$—, (b) —C(O)—CH=CH—, (c) —C(O)—$(CH_2)_q$—, (d) —$(CH_2)_q(O)$—, (e) —O—$(CH_2)_q$, (f) —O—$(CH_2)_m$—O—, (g) —CH(OH) $(CH_2)_q$—, (h) —$(CH_2)_q$CH(OH)—, (i) —CH=CH—C(O)—, (j) —(CH=CH)$_m$—, (k) —$(CH_2)_m$O— wherein m is an integer from one to six; q is an integer of zero to six; and Z is a substituent having the structure as shown in the formula page as (a) i, (b) ii, (c) iii, (d) iv, (e) v, (f) vi, (g) vii, or (h) viii, wherein n is an integer of zero to five and R may be the same or different and lower alkyl of from one to four carbons, inclusive; hydroxy, alkoxy of from one to four carbons, inclusive, halogen, or Z as defined above except that R is hydrogen; with the over all proviso that R may only be attached to a carbon and that each carbon may carry only one R; or a pharmaceutically acceptable salt thereof.

The present invention also includes a pharmaceutical composition comprising an amount of a compound of Formula I wherein $R_1$, B, m, Z, n, q, and R are as defined above effective for treating asthma, allergies, cardiovascular disorder, migraine, or an immunoinflammatory condition, in admixture with a pharmaceutically acceptable carrier.

Further, the invention is a method of treating asthma, allergies, cardiovascular disorders, migraine, or an immunoinflammatory condition by administering an antiasthma, antiallergy, cardiovascular, antimigraine, or antiimmunoinflammatory effective amount to a subject, including a human suffering therefrom, of a compound of Formula I wherein $R_1$, B, m, Z, n, q, and R are as defined above or a pharmaceutically acceptable salt thereof.

Finally, the present invention is also a novel process for the preparation of a compound of Formula I wherein $R_1$, B, m, Z, n, q, and R are as defined above which comprises reacting a compound of Formula III wherein $R_1$, B, m, Z, n, q, and R are as defined above with a compound of Formula II to obtain the compound I (see Scheme I).

DETAILED DESCRIPTION OF INVENTION

The term "lower alkyl of from one to four carbons, inclusive" as used herein includes methyl, ethyl, propyl, or butyl, and isomers thereof.

The term "lower alkoxy of from one to four carbons, inclusive" as used herein includes methoxy, ethoxy, propoxy, or butyloxy, and isomers thereof.

The term "halogen" as used herein includes, Br, Cl, F, or $CF_3$.

Preferred compounds of the present invention are compounds of the Formula I wherein B is attached in either the meta or para position and then B is (a) —$(CH_2)_m$—, (c) —C(O)—$(CH_2)_q$—, (e) —O—$(CH_2)_q$—, or (f) —O—$(CH_2)_m$—O—.

More preferred compounds of the present invention are the preferred compounds of Formula I wherein B is (a) —$(CH_2)_m$— wherein m is one through three and Z is the moiety shown as (i) wherein n is 0 or n is two when R is halo or alkyl of from one to four carbons, inclusive; wherein B is (c) —C(O)—$(CH_2)_q$— wherein q is one through three and Z is the moiety shown as (i) wherein n is zero or n is two when R is halo or alkyl of from one to four carbons, inclusive; wherein B is (e) —O—$(CH_2)_q$— wherein q is one through three and Z is the moiety shown as (i) wherein n is zero or n is two when R is halo or alkyl of from one to four carbons-, inclusive; and wherein B is (f) —O—$(CH_2)_m$—O— wherein m is two or three and Z is the moiety shown as (i) wherein n is zero or n is two when R is halo or alkyl of from one to four carbons, inclusive.

The most preferred compounds of Formula I are the more preferred compounds wherein B is (a) wherein m is three and n is zero or n is two when R is chloro or methyl; B is (c) wherein q is three and n is zero or n is two when R is chloro or methyl; B is (e) wherein q is three and n is zero or n is two when R is chloro or methyl; and B is (f) wherein m is two and n is zero or n is two when R is chloro or methyl.

The pharmacologically acceptable salts of the present invention may be those readily prepared with inorganic and organic bases, such as NaOH, KOH, Mg(OH)$_2$, Ca(OH)$_2$, NH$_4$OH, substituted ammonium salts, L-arginine, choline, N-methyl glucamine and the like.

By virtue of the activity of the compounds having the Formula I of the present invention as leukotriene D4 antagonists, and inhibitors of 5-lipoxygenase and histamine release from basophils the compounds are useful in treating asthmas and allergies as well as cardiovascular disorders, migraine, and immunoinflammatory conditions. See B. Samuelsson, "Leukotrienes: Mediators of Immediate Hypersensitivity Reactions and Inflammation, "*Science*" Vol. 220, p 568 (1983); P. J. Piper, "Leukotrienes," *Trends in Pharmaceutic Sciences*, pp 75 & 77 (1983), and J. L. Romson, et al, "Reduction of the Extent of Ischemic Myocardial Injury by Neutrophil Depletion in the Dog," *Circulation*, Vol. 67, pp 1016 (1983).

Additionally, the activity, of the compounds having the Formula I of the present invention is determined by the well known leukotriene receptor binding assay that is described by R. F. Bruns, W. J. Thomsen and T. A. Pugsley in *Life Sciences*, 33, 645 (1983) or the Herxheimer in vivo antiallergy test described in H. Herxheimer, *J. Physiol.* (London), Vol. 177, p. 251 (1952).

The antiasthma and antiallergic activity provides methods of treatment for hypersensitivity reaction having broad symptoms. For example, the symptons may include dermatitis, lacrimation, nasal discharge, coughing, sneezing, nausea, vomiting, diarrhea, difficulty in breathing, pain, inflammation, and in severe cases, anaphylactic shock and circulatory collapse. The symptoms may be found in man as well as other animals suffering from bronchial asthma, seasonal pollinosis (e.g., hayfever), allergic rhinitis, urticoria, allergic conjunctivitis, food allergies, and anaphylactoid reactions.

Likewise, the activity of the compounds of Formula I provides a method of treatment for cardiovascular disorders, particularly ischemia and myocardial infarctions. The symptoms of a subject having a cardiovascular disorder may be determined by special diagnostic procedures directed to subjects having a history, general physical appearance, and then detailed deviations from normal appearances suggesting a cardiovascular disorder. Such disorders are also found in man as well as other mammals. Symptoms of the disorders are described extensively in *The Merck Manual* 14th ed, (1982).

Further, method of treatment is provided by the compounds of Formula I herein for migraine and immunoinflammation. The symptoms requiring treatment for these purposes are readily recognized, particularly for migraine in man and/or immunoinflammation in man as well as other mammals.

Pharmaceutical compositions which also are the present invention are prepared from the compound of Formula I and salts thereof described as the present invention having inert pharmaceutical carriers. The compositions may be either solid or liquid.

A physician or veterinarian of ordinary skill readily determines a subject who is exhibiting symptoms described herein. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area (e.g., in the form of eye drops or by inhalation). For the treatment of asthma or allergies such as erythema, the compounds of the present invention may also be administered topically in the form of ointments, creams, gels, or the like.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

Initial dosages of the compounds of the invention having Formula I are ordinarily in the area of 1.0 mg/kg up to 500.0 mg/kg per day orally, preferably 5.0 mg/kg to 10.0 mg/kg per dose orally, given from one to four times daily or as needed. When other forms of administration are employed equivalent doses are administered.

Generally, the compounds, having the Formula I wherein $R_1$, B, m, Z, n, q and R are as defined above are prepared by stirring a compound of Formula III wherein $R_1$, B, m, Z, n, q and R are as defined above with diphenic acid anhydride in an inert organic solvent, such as dichloromethane, tetrahydrofuran, toluene, 1,2-dichloroethane, and the like at about room temperature or at reflux for from 30 minutes to overnight, preferably less than five hours (See Scheme I).

The synthesis of the various anilines of the Formula III as defined above are carried out using the procedures analogous to those described either by E. P. Kohler and H. M. Chadwell, Organic Synthesis Coll. Vol. 1, 78 (1941) and H. F. Hodson, J. W. T. Lowlands, and C. M. Leaver, EPO28305 (1979) or G. Markl and A. Merz, *Synthesis*, 295 (1973), and *Synthetic Communications* (1976), 6, 53, or a modification of these methods. Nitrations were done according to the procedures of G. Powell and F. R. Johnson, *Org. Syn.*, Coll, Vol. II, p 44, or R. E. Buckles and M. P. Bellis, *Org. Syn.*, Coll. Vol. IV, p 722.

Method A (Scheme $II_1$ and $II_2$)

Generally, the preparation of the compounds of Formula $III_1$ or $III_2$ wherein R and n are as defined above is the method as shown in SCHEMES $II_1$ or $II_2$. The necessary benzyl triphenylphosphonium halide salts of Formula $IV_1$ or $IV_2$ wherein R and n are as defined above are prepared by the procedure analogous to that described by R. Ketchan, D. Jambotkar, and L. Martenelli, *J. Org. Chem.*, 27, 466 (1962) and *Synthetic Commun.*, 6, 53 (1976). The aldehydes are either purchased or prepared by a condensation of acetaldehyde and a substituted benzaldehyde giving the necessary cinnamaldehyde of Formula $V_1$ wherein R and n are as defined above and Formula $V_2$. The aromatic aldehyde $V_1$ or $V_2$ and benzyltriphenylphosphonium salt $IV_1$ or $IV_2$ are coupled using n-butyllithium as the base in THF or toluene at a temperature of from $-10°$ C. to reflux, preferably at room temperature. Reduction of the nitro group and double bond in the coupled product is accomplished simultaneously using about 50 psig hydrogen and a Raney Nickel catalyst under standard hydrogenation conditions.

Method B

Generally, the necessary aryl- or aralkyl-phenylketones of Formula $XII_4$, wherein R and n are defined above used as starting materials are prepared by obvious routes or as described below or purchased directly.

To prepare meta-substituted aniline side-chains the aryl or aralkyl phenyl ketone $XII_4$ is nitrated directly at $-15°$ to $0°$ C. in acetic anhydride and a nitric acid solution up to room temperature then reduced to the anilines in a solvent such as alcohol or ethers at room temperature and used directly or subjected to Wolff-Kischner reduction of the ketone (see *The Merck Index*, 10th Ed, pp ONR-97) and then reduced to the aniline.

The parasubstituted aniline side chains are prepared by performing a Wolff-Kischner reduction (see *The Merck Index*, 10th Ed, pp ONR-97) on the aryl- or aralkyl-phenylketones XII followed by nitration, isolation of the pure p-isomer and reduction of the nitro group to an aniline again by a catalytic hydrogenation as cited above.

See Scheme III for preparation of both the meta- and para-substituted anilines as described above.

Alternatively, the preparation of the compound of Formula III wherein B is an alkyl of three carbons may be accomplished via a Claisen-Schmidt condensation (see *The Merck Index,* 10th Ed, pp ONR-19) of a nitroacetophenone and an aromatic aldehyde followed by reduction of the double-bond as accomplished above and the nitro group. The resultant keto-aniline could be used directly or the ketone could be removed by a Wolff-Kischner reduction cited above. This preparation is shown in Scheme IV.

Method C (see Scheme V and Scheme VI)

Generally, to prepare compounds of Formula III wherein B is $-O-(CH_2)_m-O-$ wherein m is as defined above; p-acetamido-phenol of Formula XXIII is condensed with a 1-bromo-δ-chloroalkane of Formula XXII in alcohol-ether at room temperature. This intermediate of Formula XXI is condensed with a substituted phenol of Formula $XXI_1$ wherein R and n is as defined above using NaH in DMF, THF, DMSO, or DMA to give the acetylated compound of Formula $XX_6$. This may be cleaved to the aniline using 6N HCl. (See Scheme V).

To prepare compounds of Formula III wherein B is $O-(CH_2)_q-$ wherein q is defined as above; 4-fluoro nitrobenzene is condensed with a ω-phenyl alkanol wherein q and R are defined as above in an ether solvent at room temperature or at reflux preferably at reflux to give the nitro compound of Formula $X_5$. This may be reduced to the amino compound $III_5$ by the hydrogenation methods described above (see Scheme VI).

The products of the reactions described herein are isolated by conventional means such as crystallization, extraction, distillation, chromatography, and the like.

Preparation of the compounds of Formula I wherein $R_1$ is lower alkyl of from one to four carbons, inclusive, is by methods analogous to those known in the art from the compounds of Formula I wherein $R_1$ is hydrogen.

The salts; both inorganic and organic, including esters, of compounds of Formula I described above are prepared by reacting the appropriate base or alcohol with a stoichometric equivalent of the carboxylic acid groups on the compound of Formula I.

The compounds of this invention may also exist in hydrated or solvated forms.

DESCRIPTION OF THE PREFERRED EMBODIMENTS

The process of this invention is further elaborated by the representative examples as follows.

PREPARATION OF INTERMEDIATES (See Schemes $II_1$ and $II_2$)

PREPARATION 1-SEE SCHEME $II_1$ a. 4-(Nitrophenyl)-butanal

In a round bottomed flask equipped with magnetic stirring and a nitrogen atmosphere was placed dichloromethane (500 ml) and 48.2 (0.128 mol) of pyridinium dichromate. This slurry was stirred vigorously and 25.0 g of 4-nitrophenylbutanol was added dropwise from a pressure equalizing addition funnel. The reaction was stirred overnight. The resultant brown slurry was filtered through silica gel with diethylether and the solution was concentrated to an oil by rotary-evaporation at aspirator pressure. This oil was purified by column chromatography using dichloromethane as eluent. A total of 15.4 g of the 4-(nitrophenyl)butanal was obtained as a yellow oil.

b. 4-(5-Phenylpentyl)-aniline

In a round bottomed flask equipped with magnetic stirring, a nitrogen atmosphere, thermometer, and pressure equalizing addition funnel was placed 22.13 g of benzyltriphenylphosphonium chloride and 400 ml of dry tetrahydrofuran. This slurry was cooled to <0° C. and 25.0 ml of n-butyllithium (2.4M in hexane) was added dropwise while maintaining the temperature at <5° C. After the addition of the n-butyllithium was complete, the slurry was stirred for six hours at room temperature then 11.0 g (0.057 mol) of 4-nitrophenylbutanal was added dropwise and the resultant mixture was stirred overnight. The solvent was removed by rotary-evaporation and the residue was dissolved in hot toluene (1000 ml) and filtered through silica gel and the silica gel was washed with 3:1 cyclohexane:ethylacetate. The toluene and cyclohexane/ethyl acetate was evaporated and the residue (10.2 g) was dissolved in 1/1 (v/v) tetrahydrofuran-methanol and 1.5 g of Raneynickel was added. This mixture was hydrogenated in a Parr TM shaker at three atmospheres of hydrogen. After ~15 hours a second 1.5 g portion of catalyst was added and the hydrogenation was continued. When 95% of the theoretical amount of hydrogen had been taken up the reaction was stopped and the catalyst was removed by filtration through celite. After removal of the solvent the crude product was purified by column chromatography using dichloromethane/cyclohexane. The 4-(5-phenylpentyl)aniline was obtained as a tan oil after combination of the appropriate fractions and removal of the solvents. The yield was 5.77 g.

PREPARATION 2-SEE SCHEME $II_1$ or $II_2$

Benzeneamines may be prepared from known nitrobenzenes in a manner similar to the above preparation as follows.

4-[2-(3,4-Dichlorophenyl)ethyl]benzenamine

4-[2-(3,4-dichlorophenyl)ethenyl]nitrobenzene (34.0 g, 116 mmol) and 2 g of Raney nickel in 510 ml of tetrahydrofuran were shaken under hydrogen at 15 psi (103.4 kPascal) until four equivalents of hydrogen were consumed. The catalyst was removed by filtration, and the resulting filtrate evaporated in vacuo to yield a residual tan solid. Recrystallization from hexane yielded 26.6 g (86%) of 4-[2-(3,4-dichlorophenyl)ethyl]benzenamine, mp 72°-74° C.

PREPARATION 3-SEE SCHEME $II_2$ 3,4-Dichlorocinnamaldehyde

This is prepared in a manner analogous to the method of U.S. Pat. No. 4,375,475 as follows.

In a round bottomed flask equipped with magnetic stirring and a pressure equalizing addition funnel was placed 3,4-dichlorobenzaldehyde (140.0 g, 0.8 mol) and acetaldehyde (300.0 ml, 5.36 mol) and the mixture was cooled to 5° C. Potassium hydroxide (5.1 g, 0.09 mol) was dissolved in methanol (40.0 ml) and added dropwise to the solution of 3,4-dichlorobenzaldehyde and acetaldehyde while maintaining the temperature at ≦30° C. The resulting brown solution was stirred in an ice bath for 30 minutes then acetic anhydride (400.0 ml) was added and the reaction was heated to 100° C. for 30 minutes. After cooling the reaction to 30° C. a solution consisting of 102 ml concentrated HCl and 1200 ml of water was added and the resulting mixture was heated to reflux for 30 minutes. The reaction as cooled to ice bath temperature and the brown solid was collected and allowed to crystallize from hot cyclohexane after treatment with decolorizing charcoal. This gave 111.0 g of 3,4-dichlorocinnamaldehyde, mp 100°–102° C.

The 3,4-dichlorocinnamaldehyde is then reacted with a nitrobenzyltriphenylphosphonium chloride in a manner similar to Preparation 1 b above (see Scheme $II_1$). The resulting 4-[4-(3,4-dichlorophenyl)butyl]benzamine is a compound of Formula III wherein $R_1$ is H, Z is 3,4-dichlorophenyl and B is butyl. The benzamine is for use as an intermediate as shown in Scheme I.

Other benzamines are prepared in a manner analogous to the following preparations which exemplify the Scheme VI and Scheme V.

PREPARATION I (SCHEME VI)

1-[4-(Aminophenoxy)]-2-phenyl ethane ($III_5$)

In a round bottom flask equipped with $N_2$ atmosphere, magnetic stirring, reflux condenser, heating mantle, and addition funnel was placed dry THF (50 ml) and sodium hydride (60% by water in oil, 1.6 g). To this slurry was added phenethanol (4.32 g) dropwise followed by 4-fluoronitrobenzene (in 10 ml THF). The exothermic reaction was controlled with an ice bath. The red solution was stirred overnight at room temperature then refluxed for four hours. The reaction was cooled and concentrated to dryness and the residue was partitioned between $CH_2Cl_2$ and $H_2O$. The organic layer was washed with $H_2O$, dried, and evaporated to a light yellow oil. This oil was triturated with hexane to give a light orange solid (3.2 g) [Analysis $C_{14}H_{13}NO_3$, actual in parenthesis, (243.26); 69.12 (68.90); 5.39 (5.39); 5.76 (5.71)]. The 1-(4-nitrophenoxy)-2-phenoxy)ethane of Formula $X_5$ was reduced under the standard conditions to the amino derivative. This low melting solid was analytically pure from the reaction after removal of the solvent [yield 2.5 g].

Analysis: $C_{14}H_{15}NO$ (213.28); 78.84 (77.45); 7.09 (6.69); 6.57 (6.11) (actual in parenthesis).

PREPARATION II (SCHEME V)

1-[4-acetamidophenoxy]-3-chloropropane (XXI)

In a round bottomed flask equipped with magnetic stirring, reflux condenser, and $N_2$ atmosphere was placed ethanol (500 ml), sodium hydroxide (15.0 g), 4-acetamidophenol of Formula XXIII (30.0 g), and 1-bromo-3-chloropropane of Formula XXII (47.0 g) and the mixture was refluxed overnight. Upon cooling off-white crystals were deposited and then collected. The mother liquor was evaporated to dryness and dissolved in $CH_2Cl_2$ then washed with $H_2O$, dried, and concentrated to 50 ml. A second crop of crystals were deposited. These were combined with the first crop of crystals and recrystallized from ethanol to give colorless crystals (20.3 g), mp 128°–130° C.

PREPARATION III 1-(4-Acetamidophenoxy)-3-(3,4-dichlorophenoxy)propane $XX_6$

In a round bottomed flask equipped with magnetic stirring, reflux condenser, $N_2$ atmosphere, and a heating mantle was placed DMF (80 ml) and to this was added cautiously NaH (60% by weight in oil, 1.76 g) followed by 3,4-dichlorophenol (7.15 g). This mixture was stirred for ten minutes then 1-[4-acetamidophenoxy]-3-chloropropane of Formula XXI (10.0 g) was added; and the reaction mixture heated at 80° C. overnight. The mixture was cooled and the DMF removed in vacuo. The residue was poured into ice water and the precipitated brown solid was collected by filtration. The crude product was recrystallized from ethanol to given an off white solid (9.8 g), mp 135°–7° C.

PREPARATION IV 1-(4-aminophenoxy)-3-(3,4-dichlorophenoxy)propane $III_6$

In a round bottomed flask equipped with magnetic stirring and a reflux condenser was placed 50 ml of 6N HCL solution and 1-(4-acetamidophenoxy)-3-(3,4-dichlorophenoxy)propane of Formula $XX_6$ (9.5 g) and the slurry was refluxed overnight and then cooled. The precipitated tan solid was collected and triturated with ethyl acetate to give a solid (8.0 g).

Analysis: $C_{15}H_{15}Cl_2NO_2.HCl$ (348.66); 51.67, (51.93); 4.63 (4.76); 4.02 (4.19); 30.51 (30.29) (actual in parenthesis).

The following anilines of Formula III are prepared in a manner analogous to the indicated method using appropriate starting materials.

| Name | mp | Method |
|---|---|---|
| 3-(2-(3,4-dichlorophenyl)ethyl)-aniline | 57–9 | A |
| 4-(3-(3,4-dichlorophenyl)propyl)-aniline $C_{15}H_{15}NCl_2$ (280.12) | oil | B |
| Calcd: C, 64.30; H, 5.39; N, 4.99; Cl 25.31 | | |
| Found: C, 63.77; H, 5.42; N, 5.07; Cl, 25.30 | | |
| 4-(3,4-dichlorobenzyl)-aniline $C_{13}H_{11}NCl_2$ (252.14) | oil | B |
| Calcd: C, 61.93; H, 4.40; N, 5.56; Cl 28.12 | | |
| Found: C, 61.68; H, 4.55; N, 5.52 | | |
| 2-(2-(3,4-dichlorophenyl)ethyl-aniline | 101–3 | A |
| 4-(4-(3,4-dichlorophenyl)butyl)-aniline | 50–2 | A |
| 4-(3-phenylpropyl)aniline | | |
| 3-(3,4-dichlorobenzyl)-aniline $C_{13}H_{11}NCl_2$ (252.14) | oil | B |
| Calcd: C, 61.93; H, 4.40; N, 5.56; | | |
| Found: C, 62.17; H, 4.53; N, 5.59; | | |
| 4-(4-phenylbutyl)-aniline $C_{16}H_{19}N$ (225.33) | oil | A |
| Calcd: C, 85.29; H, 8.50; N, 6.22 | | |
| Found: C, 85.40; H, 8.55; N, 6.20 | | |
| 4-(2-(3,4-dichlorophenyl)ethyl)-aniline | 72–4 | A |
| 4-(5-phenylpentyl)aniline | oil | A |

Miscellaneous intermediates are prepared in a manner analogous to the description of the indicated method using appropriate starting materials.

| Name | mp °C. | Method |
|---|---|---|
| 1-phenyl-3-(3,4-dichlorophenyl)-prop-2-enol | 120–122 | B |
| (1-benzoyl)-2-(3,4-dichlorophenyl)-ethylene | | |
| 3-(3,4-dichlorphenyl)propiophenone | 44–45 | B |
| 3-nitro-3',4'-dichlorobenzophenone | 133–5 | B |
| 1-phenyl-3-(3,4-dichlorophenyl)-propane $C_{15}H_{14}Cl_2$ (265.18) | oil | B |
| Calcd: C, 67.94; H, 5.32; Cl, 26.0 | | |
| Found: C, 68.29; H, 5.58; Cl 27.0 | | |
| 3,4-dichlorodiphenylmethane | oil | B |
| 4-nitro-3',4'-dichlorodiphenyl-methane | 95–7 | B |
| 1-(4-nitrophenyl)-3-(3,4-dichloro-phenyl)propane | 72–4 | B |
| 3-nitro-3',4'-dichlorostilbene | 150–2 | A |
| 2-nitro-3',4'-dichlorostilbene $C_{14}H_{19}NO_2Cl_2$ (294.14) | mixture of isomers | A |
| Calcd: C, 57.17; H, 3.08; N, 4.76; Cl, 24.0 | | |
| Found: C, 56.95; H, 2.99; N, 4.77; Cl, 24.0 | | |

-continued

| Name | mp °C. | Method |
|---|---|---|
| 1-(4-(nitrophenyl)-4-(3,4-dichlorophenyl-1,3-butadiene $C_{16}H_{11}NO_2Cl_2$ (320.175) Calcd; C, 60.02; H, 3.46; N, 4.37; Cl, 22.15 Found: C, 59.77; H, 3.47; N, 4.40; Cl, 22.39 | 125–135 | A |
| 1-(4-nitrophenyl)-3-phenylprop-1-ene $C_{15}H_{13}NO_2$ Calcd: C, 75.30; H, 5.48; N, 5.85 Found: C, 75.10; H, 5.70, N, 5.88 | oil | A |
| 1-(4-nitrophenyl)-4-phenyl-1,3-butadiene | 75–6 | A |

EXAMPLE 1

[1,1'-Biphenyl]-2-carboxylic acid, 2'-[[[4-[3-(3,4-dichlorophenyl)propyl]phenyl]amino]carbonyl]-

In a round bottom flask equipped with magnetic stirring reflux condenser, and heating mantle was placed diphenic acid anhydride (9.6 g, 0.043 mol), 4-[3,4-dichlorophenylpropyl]benzamine (III$_4$) (12.0 g, 0.043 mol), and 1,2-dichloroethane. The solution was refluxed for five hours then cooled to room temperature. The solution was evaporated to a foam-like material. The crude product was dissolved in hot 95% ethanol then diluted with H$_2$O (70 ml). After cooling an off-white solid was deposited. The product was collected and dried overnight at 60° C. at house vacuum to yield 19.9 g of the title compound.

Analysis: $C_{29}H_{23}Cl_2NO_3$ (504.41); 69.05 (69.33); 4.60 (4.78); 2.78 (2.88); 14.06 (14.08).

EXAMPLE 2

[1,1'-Biphenyl]-2-carboxylic acid, 2'-[[[4-[3-(3-phenylpropoxy]phenyl]amino]carboxyl]-

In a round bottomed flask equipped with magnetic stirring, reflux condenser, and heating mantle was placed 1,2-dichloroethane (30 ml), diphenic acid anhydride (0.74 g, 3.3 mmol), and 4-(3-phenylpropyloxy)-benzamine (0.75 g, 3.3 mmol) which had been prepared from the corresponding hydrochloride salt in the following manner. The hydrochloride salt (1.0 g, 3.8 mmol) was slurried in water and triethylamine (0.6 ml) was added followed by diethylether (20 ml). The ether layer was separated, dried, filtered, and evaporated to yield 0.75 g of the desired benzamine. The reaction mixture was refluxed for three hours then cooled to room temperature and concentrated to a foam-like material. The crude product was purified by column chromatography on silica gel using dichloromethane and 9/1 v/v dichloromethane/methanol as eluents. The fractions containing the product were combined and evaporated to a foam-like material. The yield was 1.2 g (mp 98°–100° C.).

Analysis: $C_{29}H_{25}NO_4$—0.05CH$_3$OH (453.12 (451.52)); 77.14 (77.00); 5.58 (5.61); 3.10 (3.09).

The following compounds of Formula I were prepared by a method analogous to either Example 1 or 2 using appropriate intermediates of Formula III wherein R$_1$, B, m, and R and n are defined in a corresponding manner. Each analysis shows the calculated values.

EXAMPLE 3

[1,1'-Biphenyl]-2-carboxylic acid, 2'-[[[4-[2-(3,4-dichlorophenyl)ethyl]phenyl]amino]carbonyl]-

Analysis: $C_{28}H_{21}Cl_2NO_3$ (490.37); 68.58 (68.40); 4.42 (4.39); 2.85 (2.95); 14.46 (14.44).

EXAMPLE 4

[1,1'-Biphenyl]-2-carboxylic acid, 2'-[[[3-[2-(3,4-dichlorophenyl)ethyl]phenyl]amino]carbonyl]-

Analysis: $C_{28}H_{21}NO_3$ (490.37); 68.54 (68.37); 4.42 (4.46); 2.85 (2.77), 14.46 (14.54).

EXAMPLE 5

[1,1'-Biphenyl]-2-carboxylic acid, 2'-[[[4-[2-(3,4-dichlorophenyl)ethyl]phenyl]methylamino]carbonyl]-

Analysis: $C_{29}H_{23}Cl_2NO_3$—0.45 $C_2H_5OH$ 504.44 (525.18); 68.38 (68.37); 4.93 (4.84); 2.67 (2.70); 13.50 (13.52)

EXAMPLE 6

[1,1'-Biphenyl]-2-carboxylic acid, 2'-[[[3-[3-(3,4-dichlorophenyl)propyl]phenyl]amino]carbonyl]

Analysis: $C_{29}H_{23}Cl_2NO_3$.0.25 $H_2O$ 508.91 (504.41); 68.44 (68.33); 4.65 (4.58); 2.75 (2.75); 14.05 (13.93).

EXAMPLE 7

[1,1'-Biphenyl]-2-carboxylic acid, 2'-[[[4-[2-(3,4-dimethoxyphenyl)ethyl]phenyl]amino]carbonyl]-

Analysis: $C_{30}H_{27}NO_5$—0.38 $C_6H_{12}$ 481.53 (513.51); 75.49 (75.21); 6.18 (6.17); 2.73 (2.73).

EXAMPLE 8

[1,1-Biphenyl]-2-carboxylic acid, 2'-[[[4-(4-chlorophenyl)ethyl]phenyl]methylamino]carbonyl]-

Analysis: $C_{29}H_{24}ClNO_3$ (469.97); 74.12 (74.30); 5.15 (5.20); 2.98 (2.99); 7.54 (7.63).

mp 185°–7° C.

EXAMPLE 9

[1,1'-Biphenyl]-2-carboxylic acid, 2'-[[4-[(3,4-dichlorophenyl)methyl]phenyl]amino]carbonyl]-

Analysis: $C_{27}H_{19}Cl_2NO_3$ (476.36); 55.35 (55.15); 3.22 (3.47); 4.96 (4.91); 25.13 (24.95).

mp 202°–4° C.

EXAMPLE 10

[1,1'-Biphenyl]-2-carboxylic acid, 2'-[[4-[2-[4-(trifluoromethyl)phenyl]ethyl]phenyl]amino]carbonyl]-

Analysis: $C_{29}H_{22}F_3NO_2$ (489.51); 71.16 (70.82); 4.53 (4.79); 2.86 (2.79); 11.64 (11.33).

mp 148°–50° C.

EXAMPLE 11

[1,1'-Biphenyl]-2-carboxylic acid, 2'-[[4-[2-[(4-chlorophenyl)ethyl]phenyl]amino]carbonyl]-

Analysis: $C_{28}H_{22}ClNO_3$ (489.51); 73.76 (74.09); 4.86 (5.17); 3.07 (2.95); 7.78 (7.85).

EXAMPLE 12

[1,1'-Biphenyl]-2-carboxylic acid, 2'-[[[2-[2-(3,4-dichlorophenyl)ethyl]phenyl]amino]carbonyl]-

Analysis: $C_{28}H_{21}Cl_2NO_3$ (490.39); 57.17 (56.95); 3.08 (2.99); 4.76 (4.77); 24.11 (24.61).

mp 193°–5° C.

EXAMPLE 13

[1,1'-Biphenyl]-2-carboxylic acid, 2'-[[[4-[2-[3,5-bis(trifluoromethyl)phenyl]ethyl]phenyl]amino]carbonyl]-

Mass Spectrum (M/Z) P+ 557, 539, 333, 180, 106.

IR KBr pellet cm$^{-1}$ 1654, 1606, 1548, 1382, 1280, 1176, 1134.

NMR (DMSO, δ), 12.78 (1H), 7.93–6.79 (15H), 3.00 (2H), 2.78 (2H).

EXAMPLE 14

[1,1'-Biphenyl]-2-carboxylic acid, 2'-[[[4-[2-[3,5-bis(1,1-dimethylethyl)-4-hydroxyphenyl]ethyl]phenyl]amino]carbonyl]-

Mass Spectrum M/Z P+ 549, 331, 313, 270, 225, 1197, 181, 152, 106.

IR KBr pellet cm$^{-1}$ 3400(b), 2958, 1702, 1603, 1539, 1437, 1235.

NMR (DMSO, δ), 8.25 (1H), 7.8–6.9 (14H), 5.03 (1H), 2.75 (4H), 1.39 (18H).

EXAMPLE 15

[1,1'-Biphenyl]-2-carboxylic acid, 2'-[[[4-[4-(3,4-dichlorophenyl)butyl]phenyl]amino]carbonyl]-

Analysis: $C_{30}H_{25}Cl_2NO_3$ (518.45); 69.50 (69.35); 4.86 (4.86); 2.70 (2.69); 13.68 (13.92).

mp 170°–4° C.

EXAMPLE 16

[1,1'-Biphenyl]-2-carboxylic acid, 2'-[[[4-(3-phenylpropyl)phenyl]amino]carbonyl]-

Analysis: $C_{29}H_{25}NO_3$ (435.52); 79.98 (80.13); 5.79 (5.81); 3.22 (3.29).

EXAMPLE 17

[1,1'-Biphenyl]-2-carboxylic acid, 2'-[[[3-[(3,4-dichlorophenyl)methyl]phenyl]amino]carbonyl]-

Analysis: $C_{27}H_{19}Cl_2NO_3$—1.5 $CH_3OH$ 476.36 (524.42); 65.27 (65.36); 4.80 (4.05); 2.67 (2.67); 13.52 (13.85).

EXAMPLE 18

[1,1'-Biphenyl]-2-carboxylic acid, 2'-[[[4-[2-(4-methylphenyl)ethyl]phenyl]amino]carbonyl]-

Analysis: $C_{29}H_{25}NO_3$—0.8 $C_2H_5OH$ 435.53 (472.38); 77.80 (77.96), 6.78 (6.42); 2.96 (2.94).

mp 110°–2° C.

EXAMPLE 19

[1,1'-Biphenyl]-2-carboxylic acid, 2'-[[[4-(4-phenyl-butyl)phenyl]amino]carbonyl]-

Analysis: $C_{30}H_{27}NO_3$ (449.27); 80.15 (79.92); 6.05 (6.30); 3.12 (3.18).

mp 70°–74° C.

EXAMPLE 20

[1,1'-Biphenyl]-2-carboxylic acid, 2'-[[4-decylphenyl)amino]carbonyl]-

Analysis: $C_{30}H_{35}NO_3$—0.25 $H_2O$ 457.64 (462.12); 77.97 (77.97); 7.74 (7.53); 3.03 (3.07).

mp 55°–60° C.

EXAMPLE 21

[1,1'-Biphenyl]-2-carboxylic acid, 2'-[[[4-(5-phenylpentyl)phenyl]amino]carbonyl]-

Analysis: $C_{31}H_{29}NO_3$ (463.55); 80.32 (80.18); 6.30 (6.32); 3.02 (2.96).

EXAMPLE 22

[1,1'-Biphenyl]-2-carboxylic acid, 2'-[[[4-[2-(pentafluorophenyl)ethyl]phenyl]amino]carbonyl]-

Analysis: $C_{28}H_{18}F_5NO_3$(511.45); 64.61 (64.58); 3.68 (3.74); 2.69 (2.73); F, 18.25 (17.89).

EXAMPLE 23

[1,1'-Biphenyl]-2-carboxylic acid, 2'-[[[2-[4-(1-oxo-3-phenyl-2-propenyl)phenyl]ethyl]amino]carbonyl]-

Analysis: $C_{31}H_{25}NO_4$—0.2 $H_2O$ 475.52 (479.12); 77.70 (77.71); 5.34 (5.34); 2.92 (2.82).

EXAMPLE 24

[1,1'-Biphenyl]-2-carboxylic acid, 2'-[[[4-[4-(2-furanyl)butyl]phenyl]amino]carbonyl]-

Analysis: $C_{28}H_{25}NO_4$—0.17 $H_2O$ 439.49 (442.55); 75.99 (75.99); 5.77 (5.94); 3.16 (3.10).

EXAMPLE 25

[1,1'-Biphenyl]-2-carboxylic acid, 2'-[[[4-(1-oxo-3-phenyl-2-propenyl)phenyl]amino]carbonyl]-

Analysis: $C_{29}H_{21}NO_4$ (447.50); 77.84 (77.54); 4.73 (4.90); 3.13 (3.06).

EXAMPLE 26

[1,1'-Biphenyl]-2-carboxylic acid, 2'-[[[4-[4-(3-pyridinyl)butyl]phenyl]amino]carbonyl]-

Analysis: $C_{29}H_{26}N_2O_3$ (450.54); 72.78 (72.68); 5.57 (5.32); 5.78 (5.85).

EXAMPLE 27

[1,1'-Biphenyl]-2-carboxylic acid, 2'-[[[4-[3-(3,4-dichlorophenyl)-1-oxopropyl]phenyl]amino]carbonyl- Analysis: $C_{29}H_{21}Cl_2NO_4$—0.25 $H_2O$ 522.90 (518.40); 66.61 (66.34); 4.14 (4.24); 2.68 (2.70).

EXAMPLE 28

[1,1'-Biphenyl]-2-carboxylic acid, 2'-[[[3-[3-(3,4-dichlorphenyl)-1-oxopropyl)phenyl]amino]carbonyl]-

Analysis: $C_{29}H_{21}Cl_2NO_4$.0.13 $C_2H_4Cl_2$ 531.26 (518.40); 66.15 (66.09); 4.08 (4.31); 2.64 (2.72); 15.08 (14.50).

EXAMPLE 29

[1,1'-Biphenyl]-2-carboxylic acid, 2'-[[[4-[3-[3,4-dichlorophenoxy]propoxy]phenyl]amino]carbonyl]-

Analysis: $C_{29}H_{23}Cl_2NO_5$.0.15 $CH_2Cl_2$ 549.15 (536.41); 63.75 (63.56); 4.28 (4.44); 2.55 (2.55); 14.85 (14.75).

EXAMPLE 30

[1,1'-Biphenyl]-2-carboxylic acid, 2'-[[[4-[2-(2,5-dimethylphenoxy]ethoxy]phenyl]amino]carbonyl]-

Analysis: $C_{30}H_{27}NO_5$.0.2 $H_2O$ 481.53 (485.13); 74.27 (74.38); 5.69 (5.43); 2.89 (2.93).

EXAMPLE 31

[1,1'-Biphenyl]-2-carboxylic acid, 2'-[[[4-[2-(3,4-dichlorophenoxy)ethoxy]phenyl]amino]carbonyl]-

Analysis: $C_{28}H_{21}Cl_2NO_5$.0.5$H_2O$ 522.38 (531.39); 63.28 (63.23); 4.17 (4.17); 2.64 (2.66); 13.34 (13.80).

EXAMPLE 32

[1,1'-Biphenyl]-2-carboxylic acid, 2'-[[[4-(2-phenoxyethoxy)phenyl]amino]carbonyl]

Analysis: $C_{28}H_{23}NO_5$.0.25 $H_2O$ 453.49 (458.00); 73.47 (73.43); 5.12 (5.39); 3.06 (3.17).

EXAMPLE 33

[1,1'-Biphenyl]-2-carboxylic acid, 2'-[[[4-(3-phenoxypropoxy)phenyl]amino]carbonyl]

Analysis: $C_{29}H_{25}NO_5$.0.37 $H_2O$ 467.52 (473.81); 73.51 (73.45); 5.40 (5.32); 2.96 (2.89).

EXAMPLE 34

[1,1'-Biphenyl]-2-carboxylic acid, 2'-[[4-(1-oxo-3-phenyl]propyl)phenyl]amino]carbonyl]-

Analysis: $C_{29}H_{23}NO_4.0.78 H_2O$ 449.51 (463.56); 75.15 (75.15); 5.34 (5.06); 3.02 (2.97).

EXAMPLE 35

[1,1'-Biphenyl]-2-carboxylic acid, 2'-[[4-[2-[2-[N-methylpyrrolyl]]ethenyl]phenyl]amino]carbonyl]-

Analysis: $C_{27}H_{22}N_2O_3.0.4 H_2O$ 422.49 (429.70); 75.47 (75.44); 5.35 (5.44); 6.52 (6.50).

EXAMPLE 36

[1,1'-Biphenyl]-2-carboxylic acid, 2'-[[4-[2-[2-furyl]ethyl]phenyl]amino]carbonyl]-

Analysis: $C_{26}H_{21}NO_4$ (411.40); 75.89 (75.58); 5.14 (5.37); 3.40 (3.38).

EXAMPLE 37

[1,1'-Biphenyl]-2-carboxylic acid, 2'-[[4-[3-[(3,4-dimethoxyphenyl)-3-oxopropyl]phenyl]amino]carbonyl]-

Analysis: $C_{31}H_{27}NO_6.0.5 C_6H_{12}$ 509.58 (551.66); 74.03 (74.11); 6.03 (7.32); 2.32 (2.54).

EXAMPLE 38

[1,1'-Biphenyl]-2-carboxylic acid, 2'-[[4-[3-(1,3-benzodioxol-5-yl)-1-oxopropyl]phenyl]amino]carbonyl]-

Analysis: $C_{30}H_{23}NO_6$ 493.49; 73.01 (72.95); 4.70 (4.90); 2.84 (2.86).

EXAMPLE 39

[1,1'-Biphenyl]-2-carboxylic acid, 2'-[[4-[2-[(3,4-dihydroxyphenyl)ethyl]phenyl]amino]carbonyl]-

Analysis: $C_{28}H_{23}NO_5.0.9 H_2O$ 453.47 (469.74); 71.60 (71.66); 5.32 (5.50); 2.98 (3.06).

EXAMPLE 40

[1,1'-Biphenyl]-2-carboxylic acid, 2'-[[4-[3-[3,4-dimethoxyphenyl)-1-hydroxypropyl]phenyl]amino]carbonyl]-

Analysis: $C_{31}H_{29}NO_6.0.5 H_2O.0.5 C_2H_6O$ 511.59 (543.63); 70.70 (70.98); 6.4 (5.87); 2.57 (2.56).

EXAMPLE 41

[1,1'-Biphenyl]-2-carboxylic acid, 2'-[[4-[3-[(2,5-dimethoxyphenyl)-3-hydroxypropyl]phenyl]amino]carbonyl]-

Analysis: $C_{31}H_{29}NO_6$ 511.55; 72.78 (73.15); 5.71 (6.02); 2.74 (2.53).

EXAMPLE 42

[1,1'-Biphenyl]-2-carboxylic acid, 2'-[[4-[1-[(phenyl-1-oxo-methyl]phenyl]amino]carbonyl]-

Analysis: $C_{27}H_{19}NO_4.1.0 C_6H_{12}$ 421.43 (505.59); 78.39 (78.43); 6.18 (7.03); 2.77 (2.45).

EXAMPLE 43

[1,1'-Biphenyl]-2-carboxylic acid, 2'-[[4-[(phenoxy)-phenyl]amino]carbonyl]-

Analysis: $C_{26}H_{79}NO_4.0.5 C_2H_6O$ 409.42 (432.46); 74.98 (74.95); 5.12 (5.25); 3.24 (3.10).

Additionally, componds of Formula I are prepared by similar analogous methods as described above in Examples 1 or 2 using appropriate intermediates of Formula III wherein R, B, m, R and n are defined in a corresponding manner.

[1,1'-Biphenyl]-2-carboxylic acid, 2'-[[[4-[3-(3,4-dimethoxyphenyl)propyl]phenyl]amino]carbonyl]-,

[1,1'-Biphenyl]-2-carboxylic acid, 2'-[[[4-[4-(3,4-dimethoxyphenyl)]butyl]phenyl]amino]carbonyl]-,

[1,1'-Biphenyl]-2-carboxylic acid, 2'-[[[4-[5-(3,4-dimethoxyphenyl)pentyl]phenyl]amino]carbonyl]-,

[1,1'-Biphenyl]-2-carboxylic acid, 2'-[[[3-(3,4-dimethoxyphenyl)methyl]phenyl]amino]carbonyl]-,

[1,1'-Biphenyl]-2-carboxylic acid, 2'-[[[3-[2-(3,4-dimethoxyphenyl)ethyl]phenyl]amino]carbonyl]-,

[1,1'-Biphenyl]-2-carboxylic acid, 2'-[[[3-[3-(3,4-dimethoxyphenyl)propyl]phenyl]amino]carbonyl]-,

[1,1'-Biphenyl]-2-carboxylic acid, 2'-[[[3-[4-(3,4-dimethoxyphenyl)butyl]phenyl]amino]carbonyl]-,

[1,1'-Biphenyl]-2-carboxylic acid, 2'-[[[3-[5-(3,4-dimethoxyphenyl)pentyl]phenyl]amino]carbonyl]-,

[1,1'-Biphenyl]-2-carboxylic acid, 2'-[[[4-(3,4-dihydroxyphenyl)methyl]phenyl]amino]carbonyl]-,

[1,1'-Biphenyl]-2-carbboxylic acid, 2'-[[[4-[2-(3,4-dihydroxyphenyl)ethyl]phenyl]amino]carbonyl]-,

[1,1'-Biphenyl]-2-carboxylic acid, 2'-[[[4-[3-(3,4-dihydroxyphenyl)propyl]phenyl]amino]carbonyl]-,

[1,1'-Biphenyl]-2-carboxylic acid, 2'-[[[4-[4-(3,4-dihydroxyphenyl)butyl]phenyl]amino]carbonyl]-,

[1,1'-Biphenyl]-2-carboxylic acid, 2'-[[[4-[5-(3,4-dihydroxyphenyl)pentyl]phenyl]amino]carbonyl]-

[1,1'-Biphenyl]-2-carboxylic acid, 2'-[[[3-(3,4-dihydroxyphenyl)methyl]phenyl]amino]carbonyl]-,

[1,1'-Biphenyl]-2-carboxylic acid, 2'-[[[3-[2-(3,4-dihydroxyphenyl)ethyl]phenyl]amino]carbonyl]-,

[1,1'-Biphenyl]-2-carboxylic acid, 2'-[[[3-[3-(3,4-dihydroxyphenyl)propyl]phenyl]amino]carbonyl]-,

[1,1'-Biphenyl]-2-carboxylic acid, 2'-[[[3-[4-(3,4-dihydroxypheny)butyl]phenyl]amino]carbonyl]-,

[1,1'-Biphenyl]-2'-carboxylic acid, 2'-[[[3-[5-(3,4-dihydroxyphenyl)pentyl]phenyl]amino]carbonyl]-,

[1,1'-Biphenyl]-carboxylic acid, 2'-[[[4-(3-hydroxy-4-methoxyphenyl)methyl]phenyl]amino]carbonyl]-,

[1,1'-Biphenyl]-2-carboxylic acid, 2'-[[[4-(4-hydroxy-3-methoxyphenyl)methyl]phenyl]amino]carbonyl]-,

[1,1'-Biphenyl]-2-carboxylic acid, 2'-[[[4-[2-(3-hydroxy-4-methoxyphenyl)ethyl]phenyl]amino]carbonyl]-,

[1,1'-Biphenyl]-2-carboxylic acid, 2'-[[[4-[2-(4-hydroxy-3-methoxyphenyl)ethyl]phenyl]amino]carbonyl]-,

[1,1-Biphenyl]-2-carboxylic acid, 2'-[[[4-[3-(3-hydroxy-4-methoxyphenyl)propyl]phenyl]amino]carbonyl]-,

[1,1-Biphenyl]-2-carboxylic acid, 2'-[[[4-[3-(4-hydroxy-3-methoxyphenyl)propyl]phenyl]amino]carbonyl]-,

[1,1'-Biphenyl]-2-carboxylic acid, 2'-[[[4-[4-(3-hydroxy-4-methoxyphenyl)butyl]phenyl]amino]carbonyl]-,

[1,1'-Biphenyl]-2-carboxylic acid, 2'-[[[4-[4-(4-hydroxy-3-methoxyphenyl)butyl]phenyl]amino]carbonyl]-,

[1,1'-Biphenyl]-2-carboxylic acid, 2'-[[[4-[5-(3-hydroxy-4-methoxyphenyl)pentyl]phenyl]amino]carbonyl]-,

[1,1'-Biphenyl]-2-carboxylic acid, 2'-[[[4-[5-(4-hydroxy-3-methoxyphenyl)pentyl]phenyl]amino]carbonyl]-,

[1,1'-Biphenyl]-2-carboxylic acid, 2'-[[[4-[3-(3,4-dimethoxyphenyl)propoxy]phenyl]amino]carbonyl]-,

[1,1'-Biphenyl]-2-carboxylic acid, 2'-[[[4-[[4-(3,4-dimethoxyphenyl)]butyl]oxy]phenyl]amino]carbonyl]-,

[1,1'-Biphenyl]-2-carboxylic acid, 2'-[[[4-[[5-(3,4-dimethoxyphenyl)pentyl]oxy]phenyl]amino]carbonyl]-,

[1,1'-Biphenyl]-2-carboxylic acid, 2'-[[[3-(3,4-dimethoxyphenyl)methoxyphenyl]amino]carbonyl]-,

[1,1'-Biphenyl]-2-carboxylic acid, 2'-[[[3-[2-(3,4-dimethoxyphenyl)ethoxy]phenyl]amino]carbonyl]-,

[1,1'-Biphenyl]-2-carboxylic acid, 2'-[[[3-[3-(3,4-dimethoxyphenyl)propoxy]phenyl]amino]carbonyl]-,

[1,1'-Biphenyl]-2-carboxylic acid, 2'-[[[3-[[4-(3,4-dimethoxyphenyl)butyl]oxy]phenyl]amino]carbonyl]-,

[1,1'-Biphenyl]-2-carboxylic acid, 2'-[[[3-[[5-(3,4-dimethoxyphenyl)pentyl]oxy]phenyl]amino]carbonyl]-,

[1,1'-Biphenyl]-2-carboxylic acid, 2'-[[[4-(3,4-dihydroxyphenyl)methoxy]phenyl]amino]carbonyl]-,

[1,1'-Biphenyl]-2-carboxylic acid, 2'-[[[4-[2-(3,4-dihydroxyphenyl)ethoxy]phenyl]amino]carbonyl]-,

[1,1'-Biphenyl]-2-carboxylic acid, 2'-[[[4-[3-(3,4-dihydroxyphenyl)propoxy]phenyl]amino]carbonyl]-,

[1,1'-Biphenyl]-2-carboxylic acid, 2'-[[[4-[[4-(3,4-dihydroxyphenyl)butyl]oxy]phenyl]amino]carbonyl]-,

[1,1'-Biphenyl]-2-carboxylic acid, 2'-[[[4-[[5-(3,4-dihydroxyphenyl)pentyl]oxy]phenyl]amino]carbonyl]-,

[1,1'-Biphenyl]-2-carboxylic acid, 2'-[[[3-(3,4-dihydroxyphenyl)methoxy]phenyl]amino]carbonyl]-,

[1,1'-Biphenyl]-2-carboxylic acid, 2'-[[[3-[2-(3,4-dihydroxyphenyl)ethoxy]phenyl]amino]carbonyl]-,

[1,1'-Biphenyl]-2-carboxylic acid, 2'-[[[3-[3-(3,4-dihydroxyphenyl)propoxy]phenyl]amino]carbonyl]-,

[1,1'-Biphenyl]-2-carboxylic acid, 2'-[[[3-[[4-(3,4-dihydroxyphenyl)butyl]oxy]phenyl]amino]carbonyl]-,

[1,1'-Biphenyl]-2'-carboxylic acid, 2'-[[[3-[[5-(3,4-dihydroxyphenyl)pentyl]oxy]phenyl]amino]carbonyl]-,

[1,1'-Biphenyl]-2-carboxylic acid, 2'-[[[4-(3-hydroxy-4-methoxyphenyl)methoxy]phenyl]amino]carbonyl]-,

[1,1'-Biphenyl]-2-carboxylic acid, 2'-[[[4-(4-hydroxy-3-methoxyphenyl)methoxy]phenyl]amino]carbonyl]-,

[1,1'-Biphenyl]-2-carboxylic acid, 2'-[[[4-[2-(3-hydroxy-4-methoxyphenyl)ethoxy]phenyl]amino]carbonyl]-,

[1,1'-Biphenyl]-2-carboxylic acid, 2'-[[[4-[2-(4-hydroxy-3-methoxyphenyl)ethoxy]phenyl]amino]carbonyl]-,

[1,1-Biphenyl]-2-carboxylic acid, 2'-[[[4-[3-(3-hydroxy-4-methoxyphenyl)propoxy]phenyl]amino]carbonyl]-,

[1,1'-Biphenyl]-2-carboxylic acid, 2'-[[[4-[3-(4-hydroxy-3-methoxyphenyl)propoxy]phenyl]amino]carbonyl]-,

[1,1'-Biphenyl]-2-carboxylic acid, 2'-[[[4-[[4-(3-hydroxy-4-methoxyphenyl)butyl]oxy]phenyl]amino]carbonyl]-,

[1,1'-Biphenyl]-2-carboxylic acid, 2'-[[[4-[[4-(4-hydroxy-3-methoxyphenyl)butyl]oxy]phenyl]amino]carbonyl]-,

[1,1'-Biphenyl]-2-carboxylic acid, 2'-[[[4-[[5-(3-hydroxy-4-methoxyphenyl)pentyl]oxy]phenyl]amino]carbonyl]-,

[1,1'-Biphenyl]-2-carboxylic acid, 2'-[[[4-[[5-(4-hydroxy-3-methoxyphenyl)pentyl]oxy]phenyl]amino]carbonyl]-.

Likewise, using the above generally described procedures the following compounds as prepared.

1,1'-Biphenyl-2-carboxylic acid, 2'-[[[4-[3-phenyl-3-oxopropyl]phenyl]amino]carbonyl]-, 1,1'-Biphenyl-2-carboxylic acid, 2'-[[[4-[3-(3-trifluoromethylphenyl)-1-oxo-propyl]phenyl]amino]carbonyl]-, 1,1'-Biphenyl-2-carboxylic acid, 2'-[[[4-[benzyloxy]phenyl]amino]carbonyl]-, 1,1'-Biphenyl-2-carboxylic acid, 2'-[[[4-[2-phenylethoxy]phenyl]amino]carbonyl]-, 1,1'-Biphenyl-2-carboxylic acid, 2'-[[[4-[4-phenylbutyloxy]phenyl]amino]carbonyl]-, 1,1'-Biphenyl-2-carboxylic acid, 2'-[[[4-[2-phenoxy-1-oxoethyl]phenyl]amino]carbonyl]-, 1,1'-Biphenyl-2-carboxylic acid, 2'-[[[4-[2-phenyl-2-oxo-ethoxy]phenyl]amino]carbonyl]-.

[1,1'-Biphenyl]-2-carboxylic acid, 2'-[[[4-[3-(3,4-dichlorophenyl)propoxy]phenyl]amino]carbonyl]-.

The usefulness of the compounds of the present invention, particularly as antiasthma and antiallergy agents is demonstrated by their effectiveness in various standard pharmacological test procedures. A description of each procedure follows.

BINDING OF $^3$H-LEUKOTRIENE D$_4$ TO GUINEA PIG LUNG MEMBRANES (RBL)

Materials

[14,15-$^3$H]leukotriene D$_4$ ($^3$H-LTD$_4$) (25 Ci/mmol and 40 Ci/mmol) is purchased from New England Nuclear. Unlabeled LTC$_4$ is a gift of Ono Pharmaceuticals (Japan). LTC$_4$, LTD$_4$, and LTE$_4$ are purchased as methyl esters from Paesel GmbH (Frankfurt, W. Germany). Concentrations of the Paesel leukotrienes are calculated from their absorbance at 280 nm. Leukotriene esters are saponified overnight under N$_2$ in 3.3% potassium carbonate at room temperature. Tritiated leukotrienes are stored as received from New England Nuclear at $-20°$ C. Ono LTC$_4$ (5 $\mu$g/ml) is stored at $-60°$ C. in phosphate buffer pH 6.8. Saponified Paesel leukotrienes are stored at $-60°$ C. in 3.3% potassium carbonate (pH 9.0-9.5). Aliquots of leukotrienes are taken from stock solutions immediately after thawing, after which the stock solutions are immediately refrozen. 2-Amino-2-(hydroxymethyl)-1,3-propanediol (Tris) is Sigma pH 7.7 pre-set crystals, and dimethylsulfoxide in Aldrich Gold Label.

Preparation of crude lung membranes

Two pairs of lungs (1.3 g) from freshly sacrificed 300 g male guinea pigs (older animals gave substantially lower binding) from Kuiper Rabbit Farm, Gary, IN are disrupted with a Polytron PT 10 (setting 4) for 30 seconds in 20 ml ice-cold 50 mM Tris adjusted with HCl to pH 7.7 at 25° C. (Tris buffer), filtered through a single layer of gauze to remove connective tissue, and centrifuged at 50,000 xg for ten min. The pellet is resuspended by homogenization with a Polytron in 20 ml Tris buffer, centrifuged at 50,000 xg for ten min., resuspended, incubated at 37° C. for 30 minutes, and centrifuged again. The final pellet is resuspended in Tris buffer and either used fresh or stored at $-70°$ C.

Binding assay

All incubations are in triplicate for 60 minutes at 25° C. in 12×75 mm polystyrene tubes containing 1 ml Tris buffer with 20 mg original tissue wet weight of guinea pig lung membranes, 0.2 nM $^3$H-LTD$_4$ (6,000–11,000 cpm), 10 mM MgCl$_2$, and 1% dimethylsulfoxide. Leukotrienes are diluted in Tris buffer. All other test compounds are dissolved at 10 mM in dimethylsulfoxide on the same day as the experiment, and diluted in dimethylsulfoxide to 100× the final incubation concentration. Control incubations receive an equal volume (10 µl) of dimethylsulfoxide; the resulting concentration of dimethylsulfoxide had no effect on binding. $^3$H-LTD$_4$ is diluted to 2 nM in Tris buffer. The membrane suspension (20 mg/0.89 ml) contains sufficient MgCl$_2$ to give 10 mM final concentration in the incubation. For test compounds with IC$_{50}$ values less than 1 µM, the order of incubations is test compound (10 µl), $^3$H-LTD$_4$ (100 µl), and membranes (0.89 ml). For test compounds with IC$_{50}$ values greater than 1 than 1 µM and limited water solubility, the order of additions is test compound, membranes, and $^3$H-LTD$_4$. All additions are performed at 0° C. Immediately after the last addition, the incubation is initiated by agitating the rack of tubes on a vortex mixer and warming to 25° C. in a water bath. Tubes are vortexed at least once more during the incubation to ensure that the membranes remained suspended. Incubations are terminated after 60 minutes by filtering under reduced pressure through 25 mm Whatman GF/B filters followed by rapid washing three times with 4 ml of ice-cold Tris buffer. Filters are added to scintillation vials with 8 ml Formula 947 (New England Nuclear), left overnight, shaken, and the radioactivity counted in a scintillation counter (efficiency 40%). Nonspecific binding, defined as binding of $^3$H-LTD$_4$ in the presence of 100 nM LTC$_4$, is 300–500 cpm for all lots of $^3$H-LTD$_4$. Binding to the filters in the absence of tissue is about 100 cpm, and is not affected by unlabeled LTC$_4$. Specific binding, defined as total binding minus nonspecific binding, varied considerably from lot to lot of $^3$H-LTD$_4$. Specific $^3$H-LTD$_4$ binding ranged from 1500 to 3000 cpm, and is greater than 80% of total binding for the better lots of $^3$H-LTD$_4$.

TO EVALUATE THE EFFECT OF EACH COMPOUNDS AS A 5-LIPOXYGENASE INHIBITOR IN COMPARISON TO STANDARD REFERENCE AGENTS IN HUMAN LEUKOCYTES (5LOA1)

The purpose of this assay is to evaluate the activity of each compound as an inhibitor of human leukocyte 5-lipoxygenase.

Arachidonic acid and calcium ionophore A23187 are obtained from Sigma (St. Louis, MO). Silica gel plates, GF are obtained from Analtech (Newark, DE). Arachidonic acid, (1-$^{14}$C) and 5-HETE ($^3$H), 5 (S)-hydroxy-6-trans, 8,11,14-cis eicosatetraenoic acid, are obtained from New England Nuclear (Boston, MA). Six percent Dextran-70 in 0.9% NaCl is obtained from Cutter Labs (Berkeley, CA).

Preparation of Leukocytes

Fresh blood from normal adult men who had not received any drugs for at least the previous five days is obtained by the Community Research Clinic (WL/PD) using venipuncture and collected into heparinized vacuotainer tubes. To every 100 ml of pooled blood is added 25 ml of dextran solution (6% dextran −70 in 0.9% sodium chloride containing 3% dextrose) and this is mixed gently in a plastic cylinder. The mixture is left to stand at room temperature for at least 90 minutes. The upper layer which is rich in leukocytes and platelets is then carefully decanted into 50 ml plastic tubes and centrifuged at about 100×g for eight minutes in an IEC centrifuge and rotor number 269 (about 600 rpm). The supernatant fluid is discarded and the pellet is resuspended in 10 ml of 0.87% ammonium chloride for exactly two minutes. This procedure is to lyse completely contaminating red blood cells. Leukocytes are then separated by centrifugation for ten minutes. The pellet is washed three times by suspension in 20 ml PBS (sodium chloride, 7.1 g; Na$_2$HPO$_4$, 1.15 g; KH$_2$PO$_4$, 0.2 g, and KCl, 0.2 g/L) and centrifuged as before. The final pellet is suspended in PBS containing 0.87 mM CaCl$_2$. Viability of the cells is then checked using trypan blue exclusion method and is found to be over 90%.

5-Lipoxygenase Enzyme Assay

Cells in suspension (0.98 ml) are incubated with or without test compounds for five minutes at 37° C. in a shaking water bath. At this time a 17 µl mixture is prepared per 1 ml of cell suspension: 100 mM arachidonic acid, 1 µl, 0.05 µCi $^{14}$C-arachidonic acid in 5 µl; 1 mM calcium ionophore A23187, 10 µl (1). This mixture is added and the incubation continued for five minutes. The reaction is stopped by adding four volumes of absolute ethanol and the mixture is kept in ice for 30 minutes. The floculated precipitate is separated by centrifugation at about 37,000×g for 20 minutes (Beckman Instruments rotor number 40). The alcohol extract is taken to dryness under a stream of nitrogen and the residue is dissolved in 100–200 µl absolute ethanol. At the time any turbidity is removed by centrifugation. An aliquot (25–50 µl) is applied onto 20×20 cm silica gel TLC plate and developed using the following solvent system: diethyl ether, petroleum ether (20°–40° C.), acetic acid (50:50:1 v/v). Zones of 1 cm apart are scraped from the TLC plate and transferred to mini-vials. Methanol (0.5 ml) is added to dissolve the radioactivity adsorbed to the silica gel and scintillation fluid (H. P., Beckman), 5 ml is then added and vials are counted in a liquid scintillation counter. A sample of $^3$H-5-HETE is applied and used for the identification of the formed 5-HETE.

Total radioactivity in the test as well as the control samples are normalized and the amount of 5-HETE present is calculated accordingly.

IC$_{50}$ values are defined as the concentrations of test agents which caused a 50% inhibition of the formation of 5-HETE as compared to control and are determined by inspection of the concentration-responsive curves.

5-LIPOXYGENASE ASSAY USING ISOLATED HUMAN LEUKOCYTES (5LOA2)

The formation of 5-HETE in human leukocytes is considered a measure of 5-lipoxygenase activity. The protocol is described in the following.

Fresh heparinized or EDTA treated human blood is mixed with 6% dextran-3% dextrose in isotonic saline in the ratio 0.25 ml dextran solution per 1.0 ml blood. After mixing the blood is allowed to sit at room temperature for about 90 minutes while the RBC's settle. During this period, the plasma is removed with a plastic pipette to nalgens tubes.

The plasma is centrifuged at 800 rpm (125 kg) on the Beckman Td-b refrigerated centrifuge to remove the platelets (which remain in the supernatant). The pellet, consisting of Leukocytes and erythrocytes, is treated with 10 ml 0.87% ammonium chloride at room temperature for four minutes, lysing the red cells. At the end of four minutes the cells are diluted with a 2× volume of phosphate buffered saline, pH 7.4, and centrifuged for ten minutes. The cells are washed three times with the phosphate buffered saline. Any of the pelleted cell matter which is not easily resuspended is discarded during the washings—the material contains platelets (12-lipoxygenase activity).

After washing, the cells are resuspended in phosphate buffered saline containing 1.0 mM calcium and 0.5 mM magnesium. After counting the cells are diluted to $1.5–2.0 \times 10^7$ leukocytes per milliliter.

To each polypropylene reaction tube is added 0.48 ml leukocytes in Ca-Mg phosphate buffered saline, pH 7.4; 1–5 µl test compound dissolved in DMSO and buffer; or DMSO for control tubes.

The tubes preincubate at 37° C. for five minutes.

The reaction is started by adding 20 µl of the following, 0.5 µl 20 mM arachidonic acid—final concentration = 20 µm; 1 µl 5 mM calcium ionophore A23187—final concentration = 10 µm; and 18.5 µl buffer.

The reaction proceeds for five minutes, then is stopped by adding 0.5 ml 0.5 mM ice cold Tris buffer, pH 8.0. The tubes are chilled on ice for ten minutes and then extracted three times with a total of 3.5 ml ethyl acetate (3.0 ml removed).

The tubes can be stored at this point. For extended storage, the tubes should be filled with nitrogen.

The ethyl acetate is evaporated with a Sorvall Speed-Vac. The residue is dissolved in ethanol. The tubes can also be stored at this point at −20° C. under nitrogen.

A portion of the ethanol solution is injected into the HPLC system for 5-HETE quantitation.

The HPLC system consists of Hewlett-Packard 1040A UV spectrophotometry system with an HP85 computer. Injections are made automatically with a Waters WISP 710B. The pump is a Spectra Physics SP8700. Peaks are measured with a Hewlett Packard 3390A integrator. An RP C-18 column is used. The solvent system is isocratic; the solvent is 70% methanol and 30% 0.01M sodium acetate, pH 5.7, pumped at 1.0 ml/min. The flow is monitored at 235 nm for 5-HETE quantitation. Using a 15 cm Alltech Nucleosil C-18 5 µM column provides for a sample turnaround time of about 16 minutes.

$IC_{50}$ is calculated as the amount of test agent that causes 50% inhibition of the formation of 5-HETE relative to the control.

SMOOTH MUSCLE RECEPTOR AGONISM—ANTAGONISM ACTIVITY EVALUATIONS IN VITRO (IVAS) ISOLATED GUINEA PIG LUNG PARENCHYMA

Isolated organs from experimental animals, have long been used to characterize the mechanism of drug activity and to elucidate the intrinsic potency and specificity of this action. The use of isolated tissues, kept viable in an oxygenated and nutritive tissue bath, has most often been used to measure specific drug activity on muscle contractile processes including the associated electrical phenomenon. The agonistic and antagonistic activity of a test drug on specialized tissue areas (receptors) associated with muscle contraction, especially in cardiovascular and visceral smooth muscle, have, in recent years, received considerable attention by many investigators.

It is generally agreed that the final decisive proof of therapeutic potential resides in the level of activity and safety of the drug in the intact animal. However, such information concerning drug action is derived prior to these final tests in animals by the characterization of this action in the isolated system which is unhindered by variability in drug absorption, distribution, and metabolism. The potency of a test compound for receptor stimulation or antagonism, for example, can easily be determined since the concentration of the compound to which the muscle cell, or specialized responsive area on this cell, is exposed can be easily controlled and correlated with the recorded activity of muscle contraction or relaxation.

The procedures described herein aare specifically concerned with the definition of a test drug action on isolated lung strips. Drug action is characterized either by an action per se on the tissues or by interaction with known smooth muscle receptor stimulants or antagonists.

Usually, the tests will be used to evaluate the ability of a test compound to antagonize the contraction induced by standard agonists in this case $LTC_4$. A relative potency is derived by comparison with one of the standard blocking drugs. In caution, relative potencies of test compounds to known standards are valid only if full dose response curves are generated and the compound compared generate parallel dose/response curves with common maxima. Appropriate "within-trial" comparisons are also necessary.

Molecular antagonists compete with the agonist for the receptor. An example of molecular antagonism would be the antihistamine activity of mepyramine relaxing a contraction of tissue produced by histamine. A physiological antagonist produces a response by action on a different receptor that causes an effect in opposition to the agonism. An example of physiological antagonism would be relaxation by the adrenoreceptor agonist isoproterenol of a tissue contraction procedure by histamine or carbachol.

Materials and Equipment

A permanent isolated bath system is used which facilitates the vertical suspension of a segment of tissue in small volume of a specific nutritive buffer. Frittered glass terminals provide dispersed bubbles of 95% oxygen and 5% carbon dioxide at the base of the individual tissue baths and the buffer reservoir. All baths and the reservoir are double-jacketed and water at 37° C. is circulated through the jacket of the baths to provide stable temperature regulation. The baths are arranged so that fresh solution from the reservoir passes through a jacketed glass coil to the base of the bath. The bubbling gas stirs the bath solution. During equilibration, fresh solution enters and excess solution is allowed to overflow. Unless a particular drug is required throughout the experiment and it is incorporated in the buffer, individual drugs are introduced directly into the bath by long hypodermic needles to the base of the bath without disturbing the tissue. Drugs are removed by rapidly draining the tissue bath from the bottom and refilling. Tissues are washed a minimum of six times. The emptying and refilling sequence takes only five seconds.

The contraction and relaxation of the smooth muscle preparation can be recorded either isotonically (change in length) or isometrically (change in tension). Isometric transducers are more sensitive and proportional. Isometric contractions are recorded electronically using Grass FT 0.03C force displacement transducers and Beckman Dynagraph recorders. The tissue is suspended vertically with one end of the segment anchored to the bottom of the bath and the other end attached to the mechanical electrical transducer muscle level. The electrical output of this transducer moves a pen on a moving chart in proportion to the force displacement.

Isolated Strip of Lung

Lung tissue is obtained from normal male guinea pigs. The heart and lungs are removed as a unit, placed in buffer, and the lungs are perfused with buffer by the spontaneously beating heart for several minutes. Distal strips of lung from the diaphragmatic lobe, approximately 0.3 cm wide and 3 cm long are removed and attached to Grass strain gage transducers. The desirable preload on the lung strips is 0.3 g of tension, with the sensitivity at 0.02 mv/cm on the amplifier and 0.5 mv/cm on the preamp, and the calibration of the chart is 1 mm=5 mg force displacement. After equilibration and priming, the tissue is ready for drug assay. When contracted with histamine, the contraction reaches the maximum within two minutes with a steady decline which takes over an hour to approach baseline. A threshold dose of histamine is approximately $3\times10^{-6}M$. At $3\times10^{-5}M$, histamine produces a contraction approximately 75% of maximum. For the leukotriene $C_4$, the contraction has a short slower ascension with a decline to a plateau after approximately seven minutes.

Test Procedures

The potency of the test compound as an antagonist is determined for a defined concentration by adding $LTC_4$ at hourly intervals for three contractions in the absence of test compound. Then drug is added and ten minutes later $LTC_4$ is again added. The inhibition of the contraction is determined by comparing the before and after drug responses.

Tissues are primed twice at a lower concentration of agonist (1 ng/ml $LTC_4$) ($a_1$) that gives a response ($r_1$) approximately 15-20% of maximum. The agonist is then increased to a concentration (2 ng/ml $LTC_4$) ($a_2$) which gives a response ($r_2$) approximately 30% of maximum. After response $r_2$ is obtained in triplicate and the tissue is washed until the tension returns to baseline, test compound at a defined concentration is added to the tissue bath. After monitoring the effect of the drug on baseline tension for ten minutes, agonist at concentration $a_2$ is given. The response (R) to agonist at concentration $a_2$ in the presence of test compound is compared to the previous response ($r_2$) without test compound.

INDUCTION AND QUANTITATION OF THE SLOW-ONSET (NONHISTAMINE) BRONCHOSPASM INDUCED BY ANTIGEN CHALLENGE IN SENSITIZED GUINEA PIGS (SRSPIG)

This guinea pig in vivo model was developed to quantitate the pulmonary effects of nonhistamine mediated, antigen-induced anaphylaxis. Mepyramine pretreatment is used to block the effects of histamine to permit quantitation of the effects of other biologically active mediators. The method is designed to detect drugs which inhibit the release or synthesis "other" mediators, such as leukotriene, thromboxane, etc., or drugs blocking the end organ effects of these mediators. When a sensitized guinea pig is exposed to the sensitizing antigen, it develops a systemic anaphylactic response characterized by increased pulmonary resistance and decreased dynamic compliance (CDYN). Pulmonary resistance is a measure of the changes in transpulmonary pressure and respiratory flow. Dynamic compliance is an expression of the relative changes in tidal volume and transpulmonary pressure. In this model, dynamic compliance is used to measure changes in the elastic propertie of the small airways and pulmonary resistance to measure constrictive responses of the large airways. In human asthma, small airway changes appear to be more closely related to the pathogenesis of disease. Thus, dynamic compliance effects will be weighted more heavily in our analysis of the changes produced by drugs. In the presence of mepyramine, the effects of histamine are blocked. The observed pulmonary effects are thought to be largely leukotriene mediated. In the guinea pig, thromboxanes may also be involved (1,2) and might augment the leukotriene response. Since leukotrienes are not preformed mediators and their effects are slow in onset, in the absence of the histamine effect, a bronchospasm is not seen until approximately 1.5-3 minutes after antigen administration. However, the leukotriene-mediated response is long lasting.

Materials and Methods

Animals: Male Hartley strain guinea pigs, weighing between 200 and 250 g on delivery, were used. The animals were supplied by the Charles River Co., Wilmington, MA.

Sensitization Procedure: Ovalbumin (2×recrystallized, Miles Laboratories Ltd.) is dissolved (0.2 mg/ml) in saline. The guinea pigs are given a single intraperitoneal injection of 0.5 ml of the stock solution to sensitize them. The animals are maintained normally for four to six weeks before use.

Anesthesia: Surgical anesthesia is induced by giving an IP injection of valium, 5 mg/kg, followed immediately by Innovar-Vet (Pitman-More), 0.7 ml/kg (IM). Each ml of Innovar-Vet contains 0.4 mg fentanyl, 20 mg droperidol, 1.8 mg methylparaben, and 0.2 mg propylparaben.

Surgical Preparation: The anesthetized guinea pig is shaved in the ventral neck region and on the right side of the thorax and affixed supine to a dissecting board. A midline incision is made in the neck and the trachea is exposed. The jugular vein is cannulated with PE 50 tubing to administer drugs and antigen. The trachea is cannulated with PE 240 tubing. If the protocol required measuring blood pressure, the carotid artery is isolated and cannulated with PE 50 tubing. A spear-like cannula is then inserted into the thorax to measure transpulmonary pressure. Needle electrodes are inserted into the musculature of each leg to record electrocardiograms.

Pulmonary Mechanics Methods: The tracheal cannula is connected inline to a Fleisch 000 pneumotachograph (factory calibration 10 cm $H_2O=22.2$ ml/sec) and a Validyne differential pressure transducer, to measure respiratory flow. Transpulmonary pressure is measured by connecting one side of a Validyne pressure transducer to the side arm of the tracheal cannula and the other side to the cannula inserted into the thorax at approximately the 5th intercostal space.

The pressure and flow signals are fed into Validyne preamplifiers and then transmitted to a pulmonary mechanics computer (Buxco). The computer computer calculates total pulmonary resistance, dynamic compliance, tidal volume, respiratory rate, and minute volume. An arterial pressure transducer (Statham P23) connected directly to the pulmonary computer is used when monitoring arterial blood pressure. The computer calculates systolic blood pressure, diastolic blood pressure, mean blood pressure and heart rate from the arterial blood pressure signal. The analog signals of the respiratory and cardiovascular parameters are also fed into a data logger (Buxco Model DL-12) which digitized the signals for output to a electric typewriter (TI

700). Simultaneously, the analog signals are fed into an eight 8 channel recorder (Beckman Dynograph) to make permanent experimental records.

Animals are mechanically ventilated using a rodent respirator (Harvard #680). In order to monitor pump pressure, a pressure transducer (Statham, Model PM131TC) is connected by a T-tube to the output side of the pump. The signal is sent directly to the Beckman recorder.

Experimental Protocol: The animal is anesthetized as described above, surgically prepared and connected to the appropriate monitoring devices. In animals that are dosed intraperitoneally, the drug is administered 30 minutes prior to antigen challenge. The animal is then attached to the respirator and the stroke volume adjusted to deliver 2.5 ml/breath at a respiratory rate of 65 breaths/min. The animal is given 1.2 mg/kg (IV) of succinyl choline (1) to arrest spontaneous breathing. One minute later, mepyramine, 2.0 mg/kg, is administered intravenously. Six minutes after the mepyramine, ovalbumin is infused over a one-minute period and the animal monitored for 15 minutes. The dose of ovalbumin is selected (3-10 mg/kg) to produce a decrease in CDYN five minutes after ovalbumin to approximately 35%±15 of the baseline value. six minutes later, all animals are dosed with the beta adrenoreceptor antagonist propranolol, 2.5 mg/kg.

Calculations and Rating System: The "baseline" values are determined by averaging the three one-minute averages of CDYN values immediately prior to ovalbumin administration. The five-minute postovalbumin % of baseline CDYN (mean ±SE) for each animal and the means for both control (A) and drug-treated groups (B) are calculated. Percent inhibition is then calculated using the formula:

$$\frac{(100 - A) - (100 - B)}{(100 - A)} = \% \text{ Inhibition of Dynamic Compliance Decrease}$$

Results

After anitigen challenge, untreated animals develop a bronchospasm. There is usually a delay of 1.5-3 minutes in the onset of the response to antigen challenge, after which, there is a rapid decline in dynamic compliance (usually to 20-50% of baseline) and an increase in pump pressure, transpulmonary pressure, and pulmonary resistance. Tidal volume might decrease slightly, but because the animal is respirated this decrease is usually small. The bronchospasm reaches its peak at four to five minutes and is stable for more than 15 minutes if no other treatments are given. The propranolol is given after six minutes to block any beta sympathomimetic tone and/or the effects of catechol release. This elicits a maximal response. Thus, animals with high sympathetic activity develop a more intense bronchoconstriction following propranolol.

HISTAMINE RELEASE FROM HUMAN BASOPHILS (HHB)

PROCEDURE OF QUANTITATING ACTIVE HISTAMINE RELEASE, AND ITS INHIBITION BY DRUGS, FROM BASOPHILS OF HUMAN BLOOD USING AN AUTOMATED FLUOROMETRIC HISTAMINE ASSAY

Mediator (histamine) release from human blood basophils is an assay which provides a model for evaluating potential antiallergy (mediator release inhibitors) compounds.

Blood from allergic donors is obtained from volunteers through the Community Research Clinic. The leukocytes are removed after Hespan ® sedimentation, washed and concentrated using calcium and magnesium free Hepes buffered saline and resuspended in Hepes Hepes buffered saline with 1 mM calcium and magnesium added back. The cells are incubated briefly at room temperature with either buffer alone (for measuring spontaneous release and challenge agent stimulated release) 6% perchloric acid (for measuring total available histamine in the cells) or drug at various concentrations. The cells are then either treated with buffer alone (to measure control spontaneous and drug effect on spontaneous release) or appropriate challenge agent (e.g., anti-IgE, antigen) mixed and incubated for 45 minutes at 37° C. in a shaking water bath. The reaction is stopped by centrifugation and the supernate is poured into autoanalyzer sample cups and samples assayed for assayed for histamine content using an automated fluorometric assay. By comparing the histamine release of drug-treated cells and the challenge agent controls, drug inhibition of mediator (histamine) release can be evaluated.

Histamine release is induced by (1) an aqueous antigen extract (short ragweed or house dust), or (2) anti-IgE antisera. Whole human blood is obtained from volunteers through the Community Research Clinic (CRC-92). Volunteers are chosen on the basis of adequate histamine release induced by antigen, or antiIgE antisera challenge. Leukocytes are incubated in vitro with the challenge agents at several concentrations. Dose-response curves for each volunteer, using each challenge agent, are generated. Test compounds are evaluated for inhibition of a near maximal response to one or more challenge agents. By including appropriate controls, it is possible to measure the effect of the test compound, at various concentrations, in several ways: (1) the effect of the compound on histamine release for each challenge agent; (2) the effect of the test compound on spontaneous release of histamine in the absence of the challenge agent (buffer alone); and (3) the effect of the test compound on the histamine assay.

Histamine is assayed using an automated continuous flow system which quantitates samples of 0.4 ml or more in volume, and concentrations of approximately 0.5 ng/ml or more. The rate of analysis is 30 samples/hour.

Methods of preparing leukocytes for this assay are described by Theuson, et al, *J. of Immunology*, Vol. 123, p. 426 (1979).

Protocol Design

Samples are run in triplicate, using either 1.5 ml polypropylene capped reaction tubes, or 5.0 ml plastic uncapped tubes. Test compounds and challenge agents are prepared in HACM buffer, as described above. Fixed volume pipettes are used.

Test compound or vehicle control is added to three reaction tubes at 1.5× the final desired concentration (i.e., 400 μl of test compound per 600 μl total reaction volume). One hundred μl of cells is added to each tube and the mixture is incubated for eight minutes at room temperature, and two minutes at 37° C. before antigen or other stimulus challenge. One hundred μl of the challenge agent at 6× the final concentration is then added, and the final mixture is incubated at 37° C. for 45 minutes in a shaking water bath. This ensures that the cell preparation is constantly in suspension. The reaction is stopped by centrifugation at 2000 RPM for three minutes at 4° C. The supernate ($\cong$500 $\mu$l) is poured into 2.0 ml autoanalyzer beakers and assayed for histamine by the fluorometric method.

In each experiment, cells from one donor are challenged with one or more of the challenge agents, according to the designed protocol and the previously determined sensitivity of the donor to particular challenge agents. Short ragweed and house dust concentrations are expressed in PNU/ml, and anti-IgE antisera in dilutions, e.g., 1E-5 (1:100,000), 3E-5 (1:30,000), and 1E-4 (1:10,000).

Calculation and Interpretation of Results

The total histamine concentration in the "total" (acid-treated) samples must be 15 ng/ml to be acceptable. Spontaneous release of histamine from the cells should not exceed 15% of the total histamine, and is frequently <5%. The maximum percentage histamine released varies with the donor. The net amount released by the challenge agent must exceed 25% of the total cellular histamine to confidently assess inhibition by test compounds. Spontaneous histamine release is subtracted from both "totals" and challenged cells to calculate net percent release. Percent inhibition is calculated using the following formula:

$$\left[ 1 - \frac{\text{Mean net \% release treated samples}}{\text{Mean net \% release for challenged control}} \right] \times 100 = \% \text{ inhibition}$$

The Automated Analyzer

The fluorometric method for histamine determination was originally described by Shore, et al[2] and has been modified to increase both its specificity and sensitivity. See R. P. Siraganian, *J. of Immunol. Res.*, Vol. 17, p. 283 (1975).

When tested by the above described procedures and shown by the notations under the acronym of each test, various compounds of the Formula I as defined above indicated activity as shown in Table 1.

TABLE 1

| Example Number | IC$_{50}$ RBL1 | 33 $\mu$M cpd HHB (antigen) | 33 $\mu$M cpd. HHB (Tripeptide) | IC$_{50}$ 5LOA (100)* | IC$_{50}$ 5LOA (20)* | SRS-PIG | IVAS |
|---|---|---|---|---|---|---|---|
| 1 | 1.0 | 72 | 72 | 9.6 | 6.7 | 51% | 90% @ 3 $\mu$M |
| 2 | 4.6 | 12 | 96 | | | 64% | |
| 3 | 4.8 | 94 | 93 | 4.6 | ° | 16% | IC$_{50}$ = 1.0 |
| 4 | 8.5 | 101 | 97 | 9.3 | | 3% | A @ 10 |
| 5 | 14.5 | 72 | 83 | 40.0 | | | |
| 6 | 1.0 | | | | | | A @ 10 |
| 7 | 88.7 | −5 | 93 | >20 | >20 | | |
| 8 | 28.7 | 67 | 111 | >20 | | | |
| 9 | 6.5 | 87 | 100 | | 19 | | |
| 10 | 9.7 | 62 | 74 | | | | |
| 11 | 13.5 | | | 12 | | | |
| 12 | 13.7 | −42 | 99 | | | | |
| 13 | 5.4 | | | | | | |
| 14 | 3.7 | 41 | 96 | | | | |
| 15 | 4.2 | @ 10 is 39 | −17 | | 4.6 | | |
| 16 | 4.3 | | 84 | | 22 | 33% | |
| 17 | 10.5 | | 97 | | | | |
| 18 | 16.5 | 60 | 98 | | | | |
| 19 | 6.7 | 59 | 90 | | 7.2 | | |
| 20 | 11.2 | | | | | | |
| 21 | 2.3 | 91 | 93 | | | 21% | |
| 22 | 10.6 | 30* ragweed | 100 | | | | |
| 23 | 50.2 | −8 | 45 | | | | |
| 24 | 10.5 | 45 | 98 | | | | |
| 25 | 14.5 | 26 | 89 | | | | |
| 26 | 36.0 | −10 | 65 | | | | |
| 27 | 0.23 | lysis | lysis | | | | |
| 28 | 5.6 | 85 | 86 | | | | |
| 29 | 5.0 | lysis | lysis | | | | |
| 30 | 1.2 | 101 | 94 | | | | |
| 31 | 2.2 | | | | | | |
| 32 | 14.7 | | | | | | |
| 33 | 2.4 | | | | | | |
| 34 | 6.5 | | | | | | |
| 35 | 30.7 | | | | | | |
| 36 | 100.0 | | | | | | |
| 37 | — | | | | | | |
| 38 | >100 | | | | | | |
| 39 | — | | | | | | |
| 40 | >100 | | | | | | |
| 41 | 56.0 | | | | | | |
| 42 | >100 | | | | | | |
| 43 | 33.6 | | | | | | |

*Concentration of exogenous arachidonic acid ($\mu$M)

Accordingly, the present invention also includes a pharmaceutical composition for treating asthma or allergies comprising an effective amount of a compound of the Formula I as defined above together with a pharmaceutically acceptable carrier.

The present invention further includes a method for treating asthma or allergies in mammals suffering therefrom comprising administering to such mammals either orally or parenterally a corresponding pharmaceutical composition containing a compound of Formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 0.1 mg to 500 mg preferably to 1 to 10 mg according to the particular application and the potency of the active ingredient. The compositions can, if desired, also contain other compatible thereapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

SCHEME I

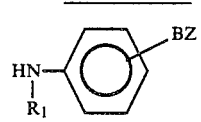

III

+

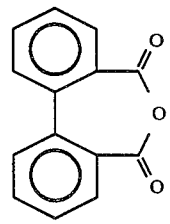

II

SCHEME II₁
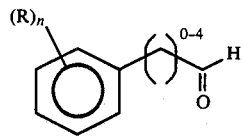
V₁
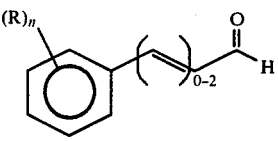
V₁
+
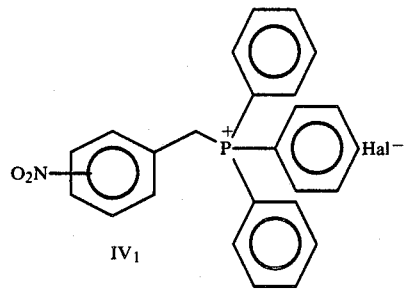
IV₁
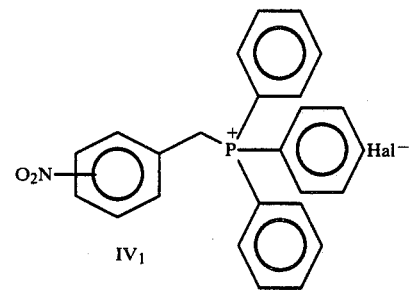
IV₁
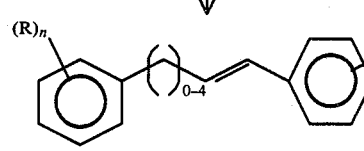
III₁
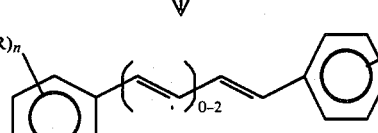
III₂
-continued
SCHEME I
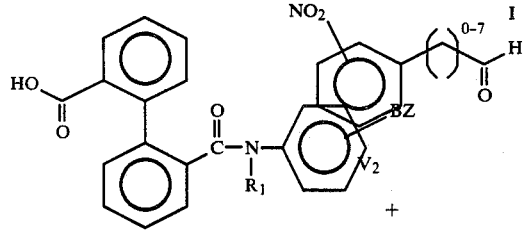
I
SCHEME II₂
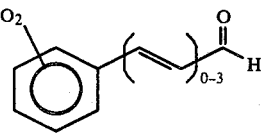
V₂
+

-continued
SCHEME II$_2$
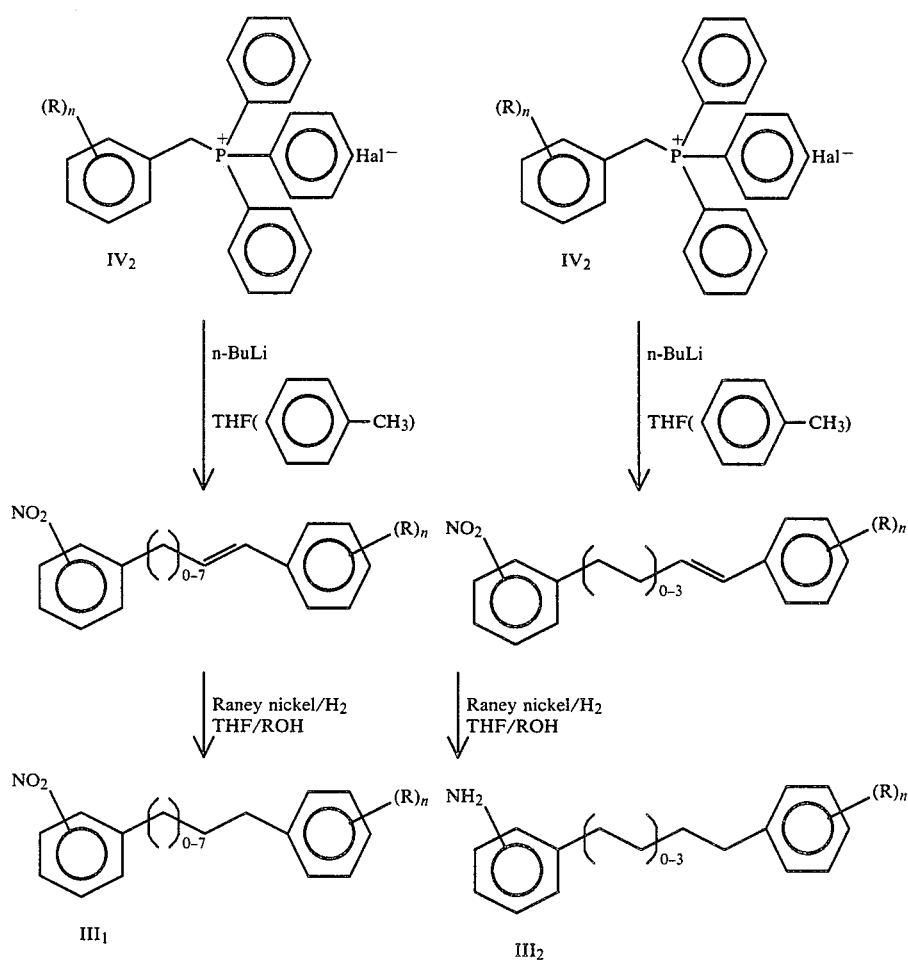
SCHEME III
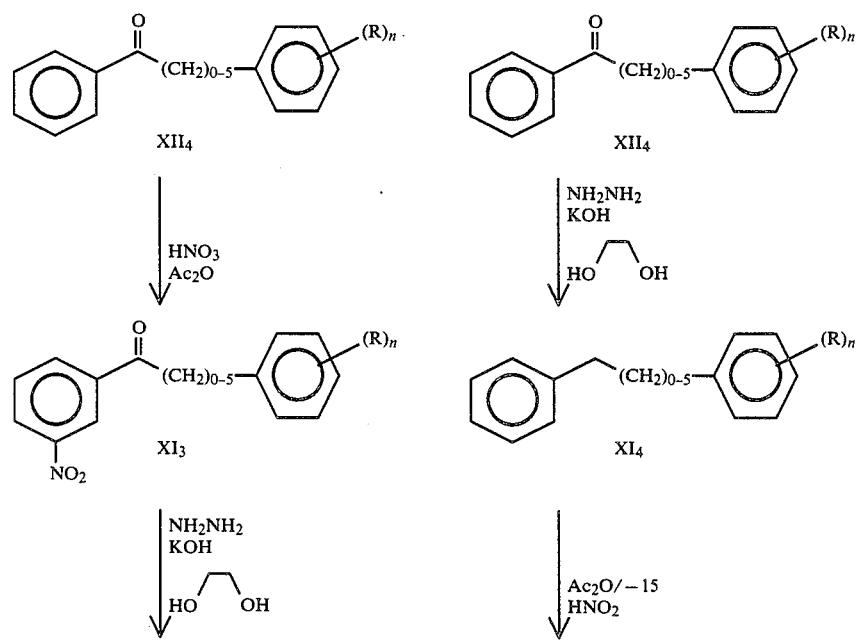

4,602,023
-continued
SCHEME III
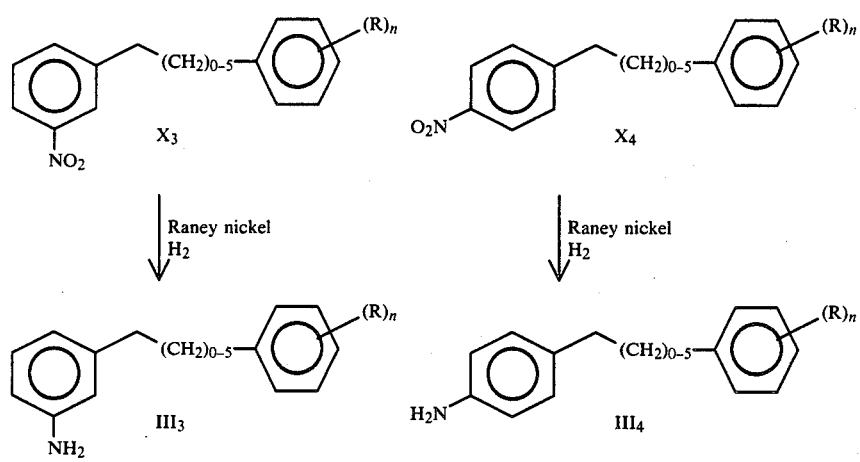
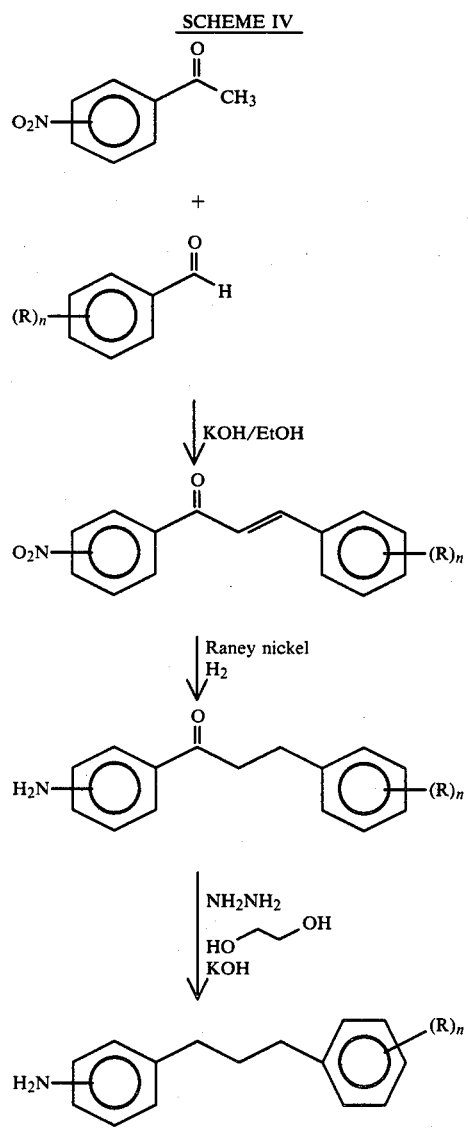
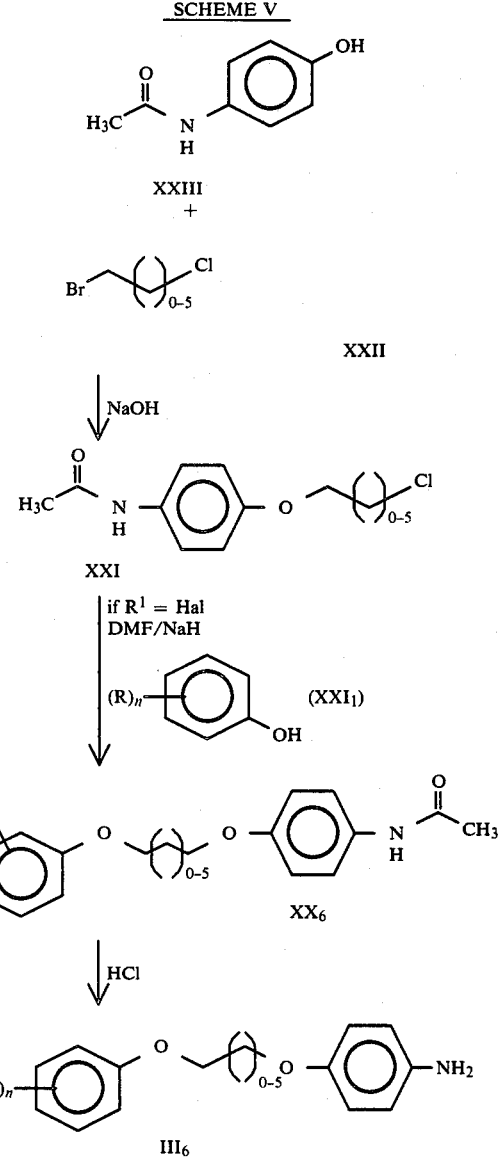

SCHEME VI

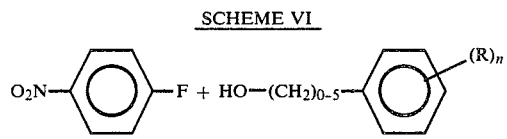 5

↓ ΔX  NaH/THF

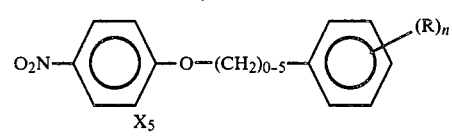  10

X₅

↓ H₂

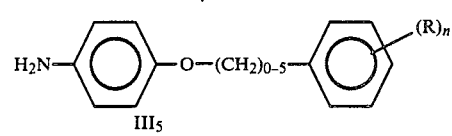  20

III₅

FORMULA

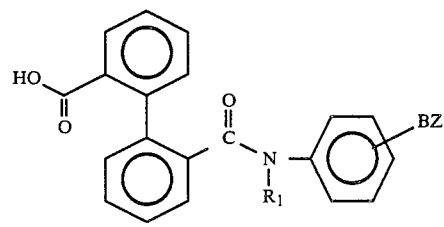  I 25

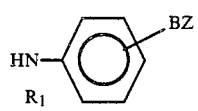  III 35

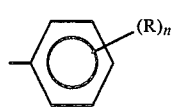  i 40

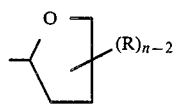  ii 45

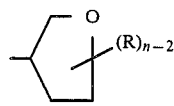  iii 50

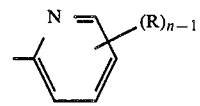  iv 55

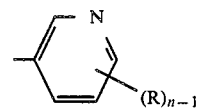  v 60

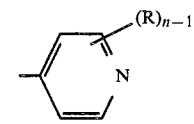  vi 65

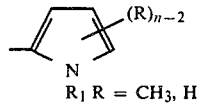  vii

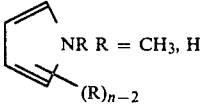  viii

We claim:

1. A compound having the formula

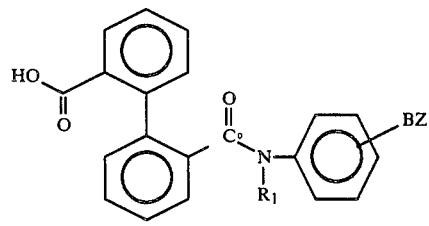  I wherein R₁ is hydrogen or lower alkyl of from one to four carbons, inclusive; B is
(a) —(CH₂)$_m$—
(b) —C(O)—CH=CH—
(c) —C(O)—(CH₂)$_q$—
(d) —(CH₂)$_q$—C(O)—
(e) —O—(CH₂)$_q$—
(f) —O—(CH₂)$_m$—O—
(g) —CH(OH)(CH₂)$_q$—
(h) —(CH₂)$_q$CH(OH)—
(i) —CH=CH—C(O)—
(j) —(CH=CH)$_m$—
(k) —(CH₂)$_q$—O— wherein m is an integer from one to six and q is an integer from zero to six and Z is (a) 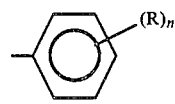  i (b) 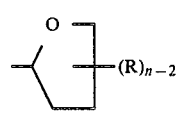  ii (c) 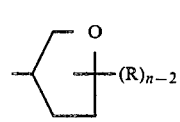  iii (d) 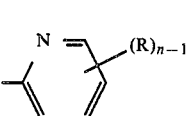  iv (e) 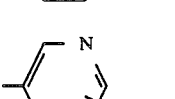  v (f) 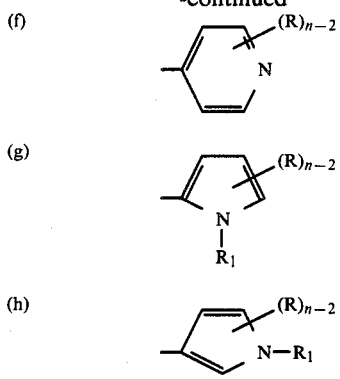 vi (g) vii (h) viii wherein n is and integer of zero to five and, R may be the same or different when n is two or more and is lower alkyl of from one to four carbons, hydroxy, alkoxy of from one to four carbons, inclusive, inclusive, halogen, or Z as defined above with the proviso that R may only be attached to a carbon and that each carbon atom may carry only one R, or pharmaceutically acceptable salts thereof; $R_1$ is lower alkyl up to butyl.

2. A compound of claim 1 wherein B is $—(CH_2)_m—$ and is attached to the position three or four of the phenylamido group in the compound of Formula I as defined above.

3. A compound of claim 1 wherein B is $—C(O)—(CH_2)_q—$ and is attached to the three or four position of the phenylamido group of the compound of Formula I as defined above.

4. A compound of claim 1 wherein B is $—O—(CH_2)_q—$.

5. A compound of claim 1 wherein B is $—O—(CH_2)_m—O—$.

6. A compound of claim 2 wherein m is one through three and Z is

wherein n is zero or n is two and R is halo or alkyl of from one to four carbons, inclusive.

7. A compound of claim 3 wherein q is one through three and Z is

wherein n is zero or n is two and R is halo or alkyl of from one to four carbons, inclusive.

8. A compound of claim 4 wherein q is one through three and Z is

wherein n is zero or n is two and R is halo or alkyl of from one to four carbons, inclusive.

9. A compound of claim 5 wherein m is one through three and Z is

wherein n is zero or n is two and R is halo or alkyl of from one to four carbons, inclusive.

10. A compound of claim 7 wherein m is three and n is zero or n is two and R is chloro or methyl.

11. A compound of claim 7 wherein q is two or three and n is zero or n is two and R is chloro or methyl.

12. A compound of claim 8 wherein q is three and n is zero or n is two and R is chloro or methyl.

13. A compound of claim 9 wherein m is two or three and n is zero or n is two and R is chloro or methyl.

14. A compound of claim 10 wherein the embodiment is [1,1'-biphenyl]-2-carboxylic acid, 2-[[[4-[3-(3,4-dichlorophenyl)propyl]phenyl]amino]carbonyl]-.

15. A compound of claim 10 wherein the embodiment is [1,1'-biphenyl]-2-carboxylic acid, 2'-[[[4-(3-phenyl)]propyl]phenyl]amino]carbonyl]-.

16. A compound of claim 11 wherein the embodiment is [1,1'-biphenyl]-2-carboxylic acid; 2'-[[[4-[3-(3,4-dichlorophenyl)-1-oxopropyl]phenyl]amino]carbonyl]-.

17. A compound of claim 11 wherein the embodiment is [1,1'-biphenyl]-2-carboxylic acid; 2'-[[[3-[3-(3,4-dichlorophenyl)-1-oxopropyl]phenyl]amino]carbonyl]-.

18. A compound of claim 11 wherein the embodiment is [1,1'-biphenyl]-2-carboxylic acid, 2'-[[[4-(1-oxo-3-phenylpropyl)phenyl]amino]carbonyl]-.

19. A compound of claim 11 wherein the embodiment is [1,1'-biphenyl]-2-carboxylic acid, 2'-[[[4-[3-3-(1,3-benzodioxol-5-yl)-1-oxopropyl]phenyl]amino]carbonyl]-.

20. A compound of claim 12 wherein the embodiment is [1,1'-biphenyl]-2-carboxylic acid, 2'-[[[4-[3-(3-phenylpropoxy)]phenyl]amino]carbonyl]-.

21. A compound of claim 12 wherein the embodiment is [1,1'-biphenyl]-2-carboxylic acid, 2'-[[[4-[3-(3,4-dichlorophenyl)propoxy]phenyl]amino]carbonyl]-.

22. A compound of claim 13 wherein the embodiment is [1,1'-biphenyl]-2-carboxylic acid, 2'-[[[4-[3-[3,4-dichlorophenoxy]propoxy]phenyl]amino]carbonyl]-.

23. A compound of claim 13 wherein the embodiment is [1,1'-biphenyl]-2-carboxylic acid, 2'-[[[4-[2-(2,5-dimethylphenoxy]ethoxy]phenyl]amino]carbonyl]-.

24. A compound of claim 13 wherein the embodiment is [1,1'-biphenyl]-2-carboxylic acid, 2'-[[[4-[2-(3,4-dichlorophenoxy)ethoxy]phenyl]amino]carbonyl]-.

25. A compound of claim 13 wherein the embodiment is [1,1'-biphenyl]-2-carboxylic acid, 2'-[[[4-(2-phenoxyethoxy)phenyl]amino]carbonyl]-.

26. A compound of claim 13 wherein the embodiment is [1,1'-biphenyl]-2-carboxylic acid, 2'-[[[4-[3-phenoxypropoxy)phenyl]amino]carbonyl]-.

27. A composition having compounds of claim 1 and a pharmaceutically acceptable carrier in unit dosage form.

28. A method of treating asthma or allergy by administering to a mammal suffering therefrom an antiasthma or antiallergy effective amount of a compound of claim 1.

29. A method of treating an immunoinflammatory condition by administering to a mammal suffering from the condition an antiimmunoinflammatory effective amount of a compound of claim 1.

30. A method of treating cardiovascular disease by administering to a mammal suffering therefrom a cardiovascular effective amount of a compound of claim 1.

31. A method of treating migraine by administering to a human suffering therefrom an antimigraine effective amount of a compound of claim 1.

* * * * *

UNITED STATES PATENT AND TRADEMARK OFFICE
CERTIFICATE OF CORRECTION

PATENT NO. : 4,602,023
DATED : July 22, 1986
INVENTOR(S) : John Kiely, et al

It is certified that error appears in the above—identified patent and that said Letters Patent is hereby corrected as shown below:

Column 37, line 19, Add "inclusive," after "carbons,

Column 37, line 20 delete the second "inclusive,"

Signed and Sealed this

Fourteenth Day of October, 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,602,023
DATED : July 22, 1986
INVENTOR(S) : John Kiely, et al

It is certified that error appears in the above—identified patent and that said Letters Patent is hereby corrected as shown below:

Column 37, line 17 change the first "and" to "an".

Signed and Sealed this

Eighteenth Day of November, 1986

Attest:

DONALD J. QUIGG

Attesting Officer  Commissioner of Patents and Trademarks